United States Patent
Goodall et al.

(10) Patent No.: US 7,262,847 B2
(45) Date of Patent: Aug. 28, 2007

(54) OPTICAL ASSEMBLY AND METHOD FOR DETECTION OF LIGHT TRANSMISSION

(75) Inventors: David Murray Goodall, York (GB); Edmund Thomas Bergstrom, York (GB); Nigel Martin Allinson, York (GB); Kevin James Moon, York (GB)

(73) Assignee: Paraytec Ltd, York (GB)

( * ) Notice: Subject to any disclaimer, the term of this patent is extended or adjusted under 35 U.S.C. 154(b) by 213 days.

(21) Appl. No.: 10/524,779

(22) PCT Filed: Aug. 15, 2003

(86) PCT No.: PCT/GB03/03591

§ 371 (c)(1), (2), (4) Date: Feb. 16, 2005

(87) PCT Pub. No.: WO2004/017061

PCT Pub. Date: Feb. 26, 2004

(65) Prior Publication Data

US 2005/0231718 A1    Oct. 20, 2005

(30) Foreign Application Priority Data

Aug. 17, 2002 (GB) .................................. 0219248.2

(51) Int. Cl.
*G01N 21/00* (2006.01)
*G01N 21/01* (2006.01)
*G01N 1/10* (2006.01)

(52) U.S. Cl. ........................ 356/344; 356/244; 356/246

(58) Field of Classification Search ................ 356/344, 356/244, 246
See application file for complete search history.

(56) References Cited

U.S. PATENT DOCUMENTS 5,239,360 A    8/1993    Moring et al.

(Continued)

FOREIGN PATENT DOCUMENTS

EP    0 594 327 A1    4/1994

(Continued)

OTHER PUBLICATIONS

Bruno A.E., et al., "On-Column Capillary Flow Cell Utilizing Optical Waveguides for Chromatographic Applications", Analytical Chemistry, American Chemical Society, vol. 16, No. 8, Apr. 15, 1989, pp. 876-883.

(Continued)

*Primary Examiner*—Roy M. Punnoose
(74) *Attorney, Agent, or Firm*—Jacobson Holman PLLC

(57) ABSTRACT

An optical assembly comprising a light source, at least one sample vessel and a detector. The detector comprises a plurality of detector locations and the vessel comprises a wall and core of relative shape and dimensions adapted to contain a sample for detection and to define at least two spatially separated transmitted light paths, a first wall path which enters and exits the vessel walls only, spatially separated from a second core path which enters and exits the vessel walls and additionally the vessel core. The spatially separated wall and core paths are coupled to individual detector locations on the detector, a module or clip-on device therefor. Methods for detection and uses of the optical assembly are also disclosed.

20 Claims, 17 Drawing Sheets

Water-filled capillary, 100 μm i.d., 194 μm o.d.

U.S. PATENT DOCUMENTS 5,312,535 A * 5/1994 Waska et al. ............... 204/603
5,582,705 A 12/1996 Yeung et al.
5,694,215 A 12/1997 Carver
5,938,908 A * 8/1999 Anazawa et al. ........... 204/603

FOREIGN PATENT DOCUMENTS

EP 0 616 211 A1 9/1994
WO WO 01/18528 A1 3/2001

OTHER PUBLICATIONS

Bergström, E.T., et al., "A Charged Coupled Device Aray Detector for Single-Wavelength and Multiwavelength . . . ", Analytical Chemistry, vol. 71, No. 19, Oct. 1999, pp. 4376-4384.

Huang, Z., et al., "Digitally Controlled Electrophoretic Focusing", Analytical Chemistry, American Chemical Society, (cited in instant specification).

* cited by examiner

Schematic diagram of experimental apparatus for parallel capillary absorbance detection Collimated illumination of rectangular CCD area, (26.6 x 6.7 mm) using light output from a 1 mm diameter fused-silica optical fibre (N.A. = 0.22) using a cylindrical and spherical fused-silica lens elements.

Detail of CCD with fibre optic stud and imaging of capillaries

Part of one CCD snapshot showing ~3 mm of 4 capillaries (100 m i.d., 194 m o.d..); the total area imaged is 6.7 x 26.6 mm. The contents of the capillaries are, 1. air, 2. water, 3 & 4 ink solution.

Water-filled capillary, 100 $\mu$m i.d., 194 $\mu$m o.d.

Water-filled capillary, 100 μm i.d., 194 μm o.d.

Water-filled capillary, 75 μm i.d., 194 μm o.d.

Water-filled capillary, 75 μm i.d., 364 μm o.d.

Electropherograms of ~16 nL 100 $\mu$M p-nitrophenol injected into each of four parallel 100 $\mu$m i.d. capillaries. Capillary length: 500 mm total, 300 mm to the detector. Separation voltage: 5000 V. Buffer: sodium phosphate pH 7.5 (15 mM sodium).

Electropherograms of 100 μM p-nitrophenol after correction for cross-talk between capillaries.

Electropherograms of ~16 nL 1 μM p-nitrophenol injected into each capillary.

Electropherograms generated by taking the average of the four traces shown in figure 11.

OPTICAL ASSEMBLY AND METHOD FOR DETECTION OF LIGHT TRANSMISSION

CROSS-REFERENCE TO RELATED APPLICATIONS

This is a nationalization of PCT/GB03/003591 filed Aug. 15, 2003 and published in English.

BACKGROUND OF THE INVENTION

The present invention relates to an optical assembly comprising a sample vessel positioned in a direct light path between a light source and a light detector, in manner to enable transmission of light through the vessel; a method for detection of light transmission through sample contained within the vessel; an apparatus comprising the assembly; more particularly an apparatus for sample analysis for example for high throughput screening (HTS) or profiling or assays, such as enzyme assays; and uses thereof in the pharmaceutical, biomedical and bioscience, agrochemical, veterinary, materials and like fields, for detection, analysis, characterization and quantification or the like of samples contained in a vessel, and optionally further collecting separated components thereof; in particular in combinatorial chemistry; in metabolomics, proteomics or genomics, assay and high throughput analysis applications, typically high sensitivity analyses, separation and/or quantification studies and for sample separation for example chromatography or electrophoresis, in particular column chromatography, capillary electrophoresis with real time or post separation analysis.

UV absorbance, fluorescence and mass spectrometry are key technologies used in separation science for analyzing species in samples. A particularly useful methodology is to look at a sample population separated by capillary electrophoresis with fluorophore labelling and fluorescence imaging, for quantification, and MS for characterizing molecules of interest.

U.S. Pat. No. 5,582,705 discloses an apparatus and system for laser induced fluorescence (LIF) detection in a multi-plexed capillary electrophoresis system. A coherent beam incident on the capillary array and emitted fluorescent light are typically perpendicular to each other in order to reduce background noise due to light scattering. A transparent portion in each capillary wall defines a transparent path extending through the array, perpendicular to the capillary. A 2D image array detector such as a charge-coupled device (CCD), preferably a charge-injection device (CID), is positioned to detect emission, and an imaging lens interposed between the capillary array and the image array detector, to optically couple the pixels to the capillary. The imaging lens may be any lens capable of transforming an image onto the pixels of the image array detector, such as a camera lens or a condenser lens. Coupling is shown in FIG. 4, of U.S. Pat. No. 5,582,705 in which every second pixel is coupled to a sidewall of the capillary and every pixel in between is coupled to an interior portion.

Fluorescence detection is limited in its application since only a limited number of molecules are naturally fluorescent and many have to be derivatized in reproducible and quantitative manner. Absorbance detection therefore has the advantage of enabling detection of a wider range of molecules. For example in enzyme assays, conducted in microtitre wells, techniques can be extended to absorbance detection of chromophoric, UV and vis absorbing substrates consumed or produced in an assay, extending the range of assay to natural as well as synthetic substrates.

However a limitation of absorbance detection lies in the operable wavelength of detection. Absorbance detection is conducted on substrates in solution. However many common solvents absorb significant amounts of light at wavelengths below ~200 nm, and the resulting solvent absorption signal distorts and masks signals resulting from the substrate to be detected. Accordingly absorbance detection is in practice limited to detection at wavelengths in excess of 190 nm, in the range UV-vis to near infra-red (NIR).

Moreover a fundamental limitation of single point absorbance detection is the impossibility of creating an image of the source at the detection point on capillary that is brighter than the light source. In "A charge coupled device array detector for single-wavelength and multi-wavelength ultraviolet absorbance in capillary electrophoresis", Bergstrom and Goodall, Pokric and Allinson, Anal. Chem. 1999, 71, 4376-4384 discloses optical detection in capillary electrophoresis by means of absorbance detection, illuminating a length of the capillary using a fiber optic bundle and using a charge coupled device (CCD) camera to image the full length of the illuminated zone. In this publication light from a fiber optic bundle is focused by a sapphire rod through the capillary core and detected on the opposite side of the capillary, by this means, increasing the target light area enabling more of the lamp output to be used and increasing the total light flux. In this case light emanates from the capillary core, so all light detected is useful and the divergent beam obtained is imaged on to the CCD.

Such a system becomes more complex once a parallel capillary array is introduced in place of the single capillary. Optics to focus light on the core of each capillary would be extremely complex and therefore irradiating both the core and walls of each capillary becomes a practical consequence.

WO 01/18528 (Yeung et al) discloses a method for analyzing multiple samples simultaneously by absorption detection of samples in a planar array of multiple containers, whereby stray light from adjacent containers is eliminated by distancing the detection means from the array, preferably at a distance greater than 10 times the diameter of a container, suitable 10-100 times the diameter for example at a distance of 1-30 cm. Containers are preferably cylindrical capillary tubes as shown in the art. The array comprises a control container if the light source is unstable. It is stated that the cross section of the container and thickness of the capillary wall are not critical. A flat field lens preferably images the containers on to the detection means.

We have now found that further improvements in absorbance detection assemblies enables increasing the total light flux through a capillary or other sample vessel, by virtue of simplification of optical components, without unduly large separation of capillary and detector which is undesirable and reduces light collection efficiency compromising path length, and therefore light intensity. The improved assembly is of particular advantage in detection in multiplexed capillary arrays and enables imaging a large area of a capillary array without the need for imaging optics. This is a significant advantage, especially when working in UV for which it is very difficult and expensive to produce suitable optics. The assembly has benefits however in both single capillary and array detection, in particular enabling a simple and improved exposure referencing and acceptably low inter-capillary cross talk without the need for optics. In addition a benefit of the assembly of the invention is that it is suitable for operation at short pathlengths, by virtue of the increased total light flux through the core of the capillary or other sample vessel, and this reduction in pathlength may lead to opportunities to conduct absorbance detection at lower wavelengths, less than 190 nm, without encountering impracticably high levels of solvent absorption.

BRIEF SUMMARY OF THE INVENTION

Accordingly there is provided in the broadest aspect of the invention an optical assembly comprising a light source, at least one sample vessel and a detector, the at least one vessel being positioned in a light path or paths created between the source and the detector in manner to enable transmission of light through the vessel wherein the light source is adapted to provide a beam of substantially collimated light, the detector comprises a plurality of detector locations and the vessel comprises a wall and core of relative shape and dimensions adapted to contain a sample for detection and to define at least two spatially separated transmitted light paths, a first wall path which enters and exits the vessel walls only, spatially separated from a second core path which enters and exits the vessel walls and additionally the vessel core, wherein the spatially separated wall and core paths are coupled to individual detector locations on the detector.

Preferably the detector is an array detector. Preferably the detector is adapted to detect and provide information on respective wall and core path light transmission. Preferably the assembly is coupled to means for displaying information on respective wall and core path light transmission or for displaying referenced information on core path light transmission, referenced against wall path light transmission.

Preferably the assembly defines a central core path and two peripheral wall paths either side thereof or an annular wall path thereabout. Paths may overlap on emerging from the vessel and at greater separations from the vessel. Preferably the wall and core paths are coupled to detector locations at a vessel outer wall to detector separation or distance d at which the paths are spatially separated, preferably giving more than 90% separation of core and wall beam fluxes. The assembly may position the vessel in two or more separate light paths to generate two or more sets of spatially separated transmitted light paths coupled to two or more detectors or detector zones.

Preferably the assembly is characterized by internal vessel dimension or path length in the range of 3 μm to 20 mm, external vessel dimension in the range 4 μm to 30 mm, refractive index of vessel wall in the range 1.3-<1.6, vessel outer wall to detector separation d in the range 10 μm to >300 mm and is for use in detecting a sample comprising analyte in solvent having refractive index in the range 1.3 to in excess of 1.5. Reference herein to a sample is to vessel contents which may comprise a single or multiple components. Multiple components may be present as a homogeneous or heterogeneous mixture, and may undergo migration with time ie may be a plurality of liquid phase components optionally including a dissolved phase component; or may include one or a plurality of analytes which it is desired to detect in one or a plurality of solvents or like bulk phase sample component, for example in the course of a chemical reaction generating or consuming a species as analyte.

In a particular advantage, the apparatus of the invention enables exposure referencing of a light beam traversing a core path of the at least one sample vessel, by a light beam traversing a wall path of the same sample vessel. The beams are spatially close, preferably adjacent, on the array detector, facilitating direct referencing as the ratio of the core beam to the wall beam. In a further advantage the two light beams are of neighboring origin whereby core and wall beams have a high probability of emanating from the same region in the light source eliminating the effects of light source fluctuations due to e.g. instability or spatial inhomogeneity. The assembly of the invention is therefore able to operate at the shot noise limit.

Preferably the light source comprises any active or passive light source, for example light may be generated at the source or it may be transmitted to the source and emanate therefrom, for example it may be transmitted by an optical fiber to the light source. Preferably the light source comprises at least one wavelength of light that is absorbed by one or more absorbing species, the absorbance of which is to be detected. For example the light source output may be coupled from a fiber optic if desired for illumination from a remote light generator or may be coupled from a point to line optical fiber for zone illumination. Coupling the output into a single optical fiber reduces noise contributions caused by fluctuations in the spatial distribution of the lamp discharge.

Light may be of wavelength in the range 160 to 1200 nm, preferably 180 or 190 to 1200 nm, corresponding to UV, UV-vis to near infra red (NIR), and is preferably in the range 180 to 700 nm corresponding to UV-vis. It is a particular advantage that the present invention enables high sensitivity absorption detection at lower path length in the range 3-500 μm and this allows operation at lower wavelengths in the range 160 to 190 nm corresponding to UV which would be impractical for absorbance detection of samples in some solvents by known techniques. Accordingly the method is more solvent independent than normal HPLC or spectrophotometric methods.

A light source may be a point or line source adapted to illuminate a section through a compact vessel or elongate vessel. A light source may be of single wavelength or multiple discrete wavelengths or wavelength range. A light source may be a tuneable light source, giving a tuneable smooth output, a line output lamp giving a very intense output at one wavelength only, a spectrum light source giving a wavelength range along the length of a line light source or the like; and may be continuous in time, or pulsed. Sources with continuous outputs are preferable when spectra are to be acquired over a wavelength range. Line sources typically provide more intense outputs at characteristic wavelengths, and are beneficial when the samples absorb at these wavelengths. Wavelength selection in the case of continuous wavelength arc lamps for example, is suitably by known technique such as interference filter positioned between the light source and collimating means or between the collimating means and the sample vessel, preferably before the collimating means. Alternatively a filter wheel or variable interference filter may be employed for sequential wavelength detection at multiple discrete wavelengths, or a wavelength dispersing device may be employed in the form of a monochromator such as a grating or prism which may be either fixed in position or continuously variable and spreads light into a spectrum, giving a varied wavelength along the length of the capillary or at right angles to the length of the capillary.

Preferably a light source comprises an iodine, zinc, cadmium or mercury lamp, or laser, as line sources; or a deuterium, xenon or tungsten lamp as continuous output lamp; or a xenon lamp as a pulsed output lamp.

More preferably the light source comprises a deuterium arc lamp (for UV light absorption) or a xenon arc lamp (for UV-vis light absorption); or comprises a tungsten lamp, more preferably a filament lamp (for visible light absorption), and the like; most preferably a high output arc lamp selected from deuterium, iodine, zinc, cadmium, mercury or xenon above; or the light source comprises a line source, preferably for the UV one of the following: iodine, zinc at 214 nm, cadmium at 229 nm, or mercury at 185, 254 or 365 nm; or the light source comprises a laser, for example in the UV a laser such as a frequency quadrupled Nd:YAG at 266 nm or Nd:YLF at 262 nm, or a He-Cd laser at 325 nm.

The light source may be expanded and recollimated by known means, for example using cylindrical and spherical lens elements and the like, preferably using an elongate lens or cylindrical optical component, such as a cylindrical fused silica lens or the like, to produce a collimated beam suitable for zone illumination of a sample vessel array.

The at least one sample vessel in the assembly of the invention may comprise a cell or conduit which may be closed or open ended and closed or open based and topped, intended for static or dynamic sample detection. The vessel may be aligned for light transmission in any suitable plane through the vessel. Suitably light transmission is through a plane perpendicular to or containing the vessel ends or base and top.

Preferably the sample vessel is a single cell or one of a plurality of cells in an array, such as a rectangular or square array, for example in a microtitre plate, well plate or multi sample plate; or is a capillary, such as a microcapillary or microfabricated channel as known in the art of microfluidic transport and separation, more preferably is a single capillary or microchannel or one of a plurality of capillaries or microchannels in a parallel array.

DETAILED DESCRIPTION OF THE INVENTION

Figure 1:
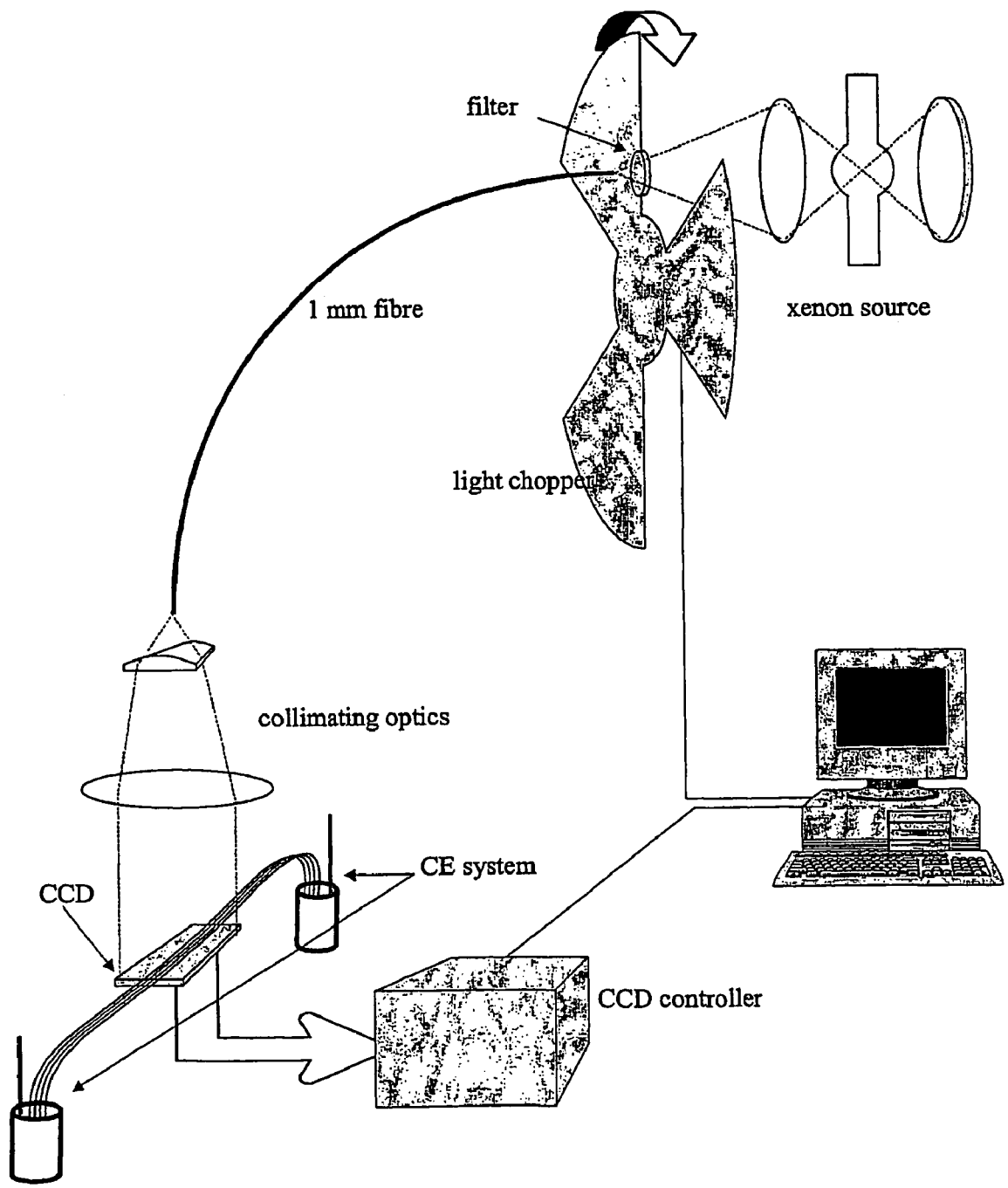
FIG. 1 shows a schematic diagram of apparatus of the invention for parallel capillary absorbance detection.

A sample vessel array is aligned in a plane perpendicular to the collimated light path whereby light passes through one vessel only. In the case that direction of illumination is in a plane containing the vessel base and top, light enters and exits each vessel through a sidewall (wall path) or enters through the top and exits through the base (core path), and in this case vessels may be aligned in a parallel or matrix array; in the case that illumination is through a plane perpendicular to the vessel ends, light enters and exits each vessel through a near side sidewall (wall path) or enters and exits through a nearside sidewall, emerges into the core, enters and exits an opposing sidewall (core path), and in this case vessels may be aligned in a parallel array, ie only one vessel deep.

For 1:1 illumination:detection, the collimated light path has dimensions substantially corresponding to the dimensions of width and length of the detector array and to a desired width and length of each sample vessel which it is desired to optically detect. Illumination:detection magnification is preferably in the range 0.8-1.5:1 in the case of arrays to avoid problems with spatial overlap of light from neighboring vessels, and is in the range 0.5-2:1 for single vessels.

Light passing through the vessel walls and core is refracted on entering and exiting the wall(s) and additionally on entering and/or exiting the core. In the case of illumination through the length of a cell or capillary, or through the cross-section of a straight walled cell or capillary, emergent wall and core light paths maintain their respective orders, ie there is substantially no cross-over or convergence of respective paths, at least at a distance d from the vessel outer wall to the detector.

In a particular embodiment of the invention the vessel of the assembly is a microfabricated device providing square cross section capillaries, and is suitable for Fabry-Perot illumination with enhanced light absorption through multiple passages through the vessel. In this case the walls of the vessel are coated with a reflective coating, within an absorption zone, whereby light enters the vessel core in an illumination zone adjacent the absorption zone, through a nearside side wall, at an angle less than 90 degrees to the wall, and at least a portion of light is reflected at the opposing wall, with repeated internal reflections throughout the absorption zone and finally emergence from the opposing wall at the end of the absorption zone. Light traversing a wall path may be similarly reflected for ease of alignment but is preferably not reflected and exposure referencing is performed as normal.

In the case of illumination through the cross-section of a curved walled cell or capillary, for example a circular cross-section capillary, emergent wall light paths reverse their respective orders about a central core light path, ie there is cross-over of respective wall paths, within a distance d to the detector. In this case the optical assembly of the invention is characterized by refraction patterns through the vessel in order to be able to spatially separate wall and core light paths. Preferably the assembly is characterized by respective outer and inner diameter of a sample vessel, and by respective refractive indices of vessel walls and of sample, whereby the wall and core paths are spatially separated as hereinbefore defined.

Preferably the refractive index of the vessel wall is greater than that of the bulk phase of any sample comprised in the core. Preferably refractive index of the wall is in the range 1.34-1.59. Preferably refractive index of bulk phase sample comprised in the core is in the range 1.32-1.48 more preferably 1.32-1.38. The refractive index of vessel wall may be modified by cladding or otherwise incorporating higher refractive index material in the vessel wall as a wall section, lens or the like.

Preferably the vessel outer wall and inner wall are additionally of shape and dimension whereby light transmitted through the core is convergent and forms a beam having an undeflected beam path, i.e. having a beam path continuous with the incident collimated light. Light passing through the wall of the sample vessel only, entering the wall at one outside wall location and exiting at a second outside wall location may be deflected or undeflected, preferably if deflected is divergent with respect to the core light path such that two classes of light paths are formed which are spatially separated.

It will be appreciated that by virtue of using a collimated light source and knowing the refractive index of the sample vessel and any sample contained therein the light path passing through any point of the vessel can be predicted for any given shape and dimension of vessel outer wall and inner wall, chosen such that collimated light passing through a square or rectangular cross section vessel, normal and parallel to respective walls, emerges substantially unrefracted and parallel; and collimated light passing through a curved or angular cross section vessel emerges uniformly divergent or convergent with a gradation in angle of refraction. This enables production of an emergent light path of high symmetry and/or uniformity, which can be manipulated for imaging and exposure referencing as hereinbefore defined.

Preferably the at least one sample vessel has a cross-section in a plane including the transmission light path, which is square or rectangular, curved circular or angular or a combination thereof and is symmetrical or asymmetrical, preferably is symmetrical. The sample vessel moreover comprises an outer and inner wall which may be of similar cross-section or shape or may be different, for example one may be circular and one square. The sample vessel wall through the cross-section may be continuous or non-continuous, for example the vessel may be open or closed and is preferably closed. A closed vessel may have a continuous wall through its cross-section or may comprise continuous base and side walls with a separate seal or lid. Preferably the outer wall is square open or closed or circular closed, and the inner wall is square or well shaped open or closed or is essentially square with microfabricated convex or concave inner wall sections acting as lens faces, or concave, convex or prism shaped outer wall sections acting as lens faces.

Preferably at least one of the outer and inner walls of the sample vessel is of circular cross-section, whereby refraction and spatial separation of core and wall beams is achieved, preferably outer and inner walls are of coaxial circular cross-section thereby defining an annular wall having outer and inner diameters such that refraction and spatial separation of core and wall beams is achieved.

It will be appreciated that sample vessel dimensions, refractive indices and/or vessel to detector distance may be selected according to the nature of vessel wall material and shape and the sample to be contained within the core in order to achieve the desired refraction and spatial separation. Accordingly the apparatus is defined by a relation of the following properties which are shown here as a flow scheme rather than as a mathematical relation:

$$\frac{i.d}{o.d.} + r.i.(\text{solvent}) + r.i.(\text{vessel}) \Rightarrow \frac{d_{\min}}{o.d.} \Rightarrow d_{\min}$$

where + infers a spatial relation which would be calculated using suitable ray tracing software to give values for vessel and assembly dimensions.

Figure 5:
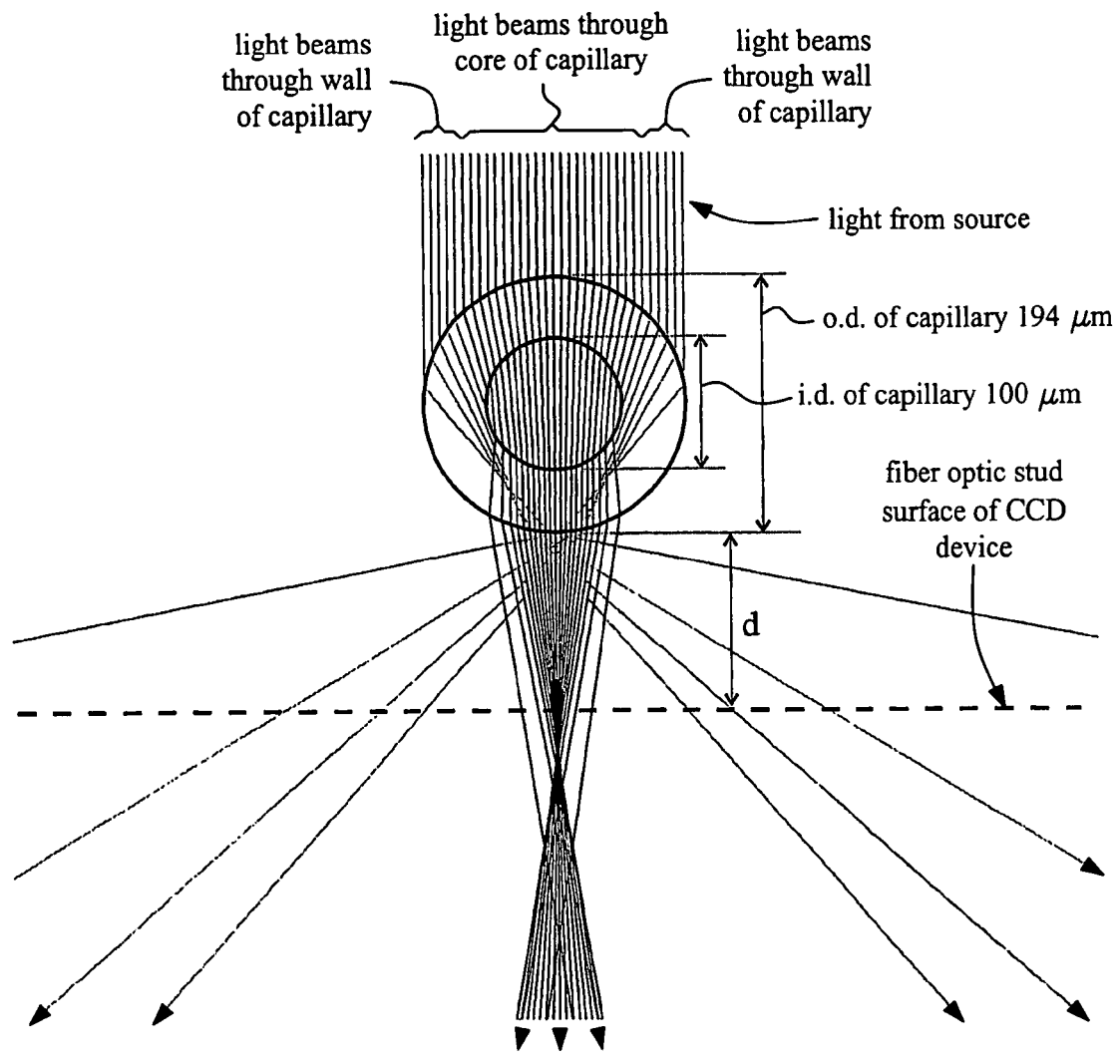
FIG. 5 shows light beam ray tracing diagram according to the invention showing light path through a water filled capillary (100 µm i.d., 194 µm o.d.). The dark rays represent the light passing through the water at the capillary center and the light rays show the light that passes only through the capillary walls. The dashed line shows the approximate position of the fiber optic stud surface.

Specifically, knowing dimensions and refractive indices, ray tracing, for example using Zemax software, may be used to produce diagrams allowing relationships between dimensions such as dmin / o.d. to be deduced. A schematic diagram showing the cross section of a cylindrical vessel and the surface of the detector is shown in FIG. 5: symbols, given here in brackets, are for the inner diameter (i.d.), the outer diameter (o.d.), and the outer wall to detector distance (d). Preferably for example for a sample vessel having circular outer and inner wall cross-section and constructed of quartz or silica, and for solvent of refractive index in the range 1.325-1.345 (encompassing for example typical reversed phase HPLC solvents methanol, water and acetonitrile), the minimum distance for spatial separation of the core and wall beams using collimated light incident on the vessel may be calculated from values given in Table 1. For example, for a ratio i.d./o.d.=0.50, the minimum value of d/o.d. to achieve beam separation (defined as >90% separation of core and wall beam fluxes) is 0.5. For a capillary with actual dimensions corresponding to this criterion, e.g. i.d. 100 µm and o.d. 194 µm, the minimum value of d/o.d. is 0.5 and thus the minimum value of d is 100 µm.

The advantage of having as high an i.d/o.d as possible is to have a low value of d/o.d., in order to minimize detector cross-talk between adjacent vessels.

Values of d/o.d. greater than the minimum are permissible, but the greater the value, the more the constraints on how close the vessels can be positioned.

Figure 6:
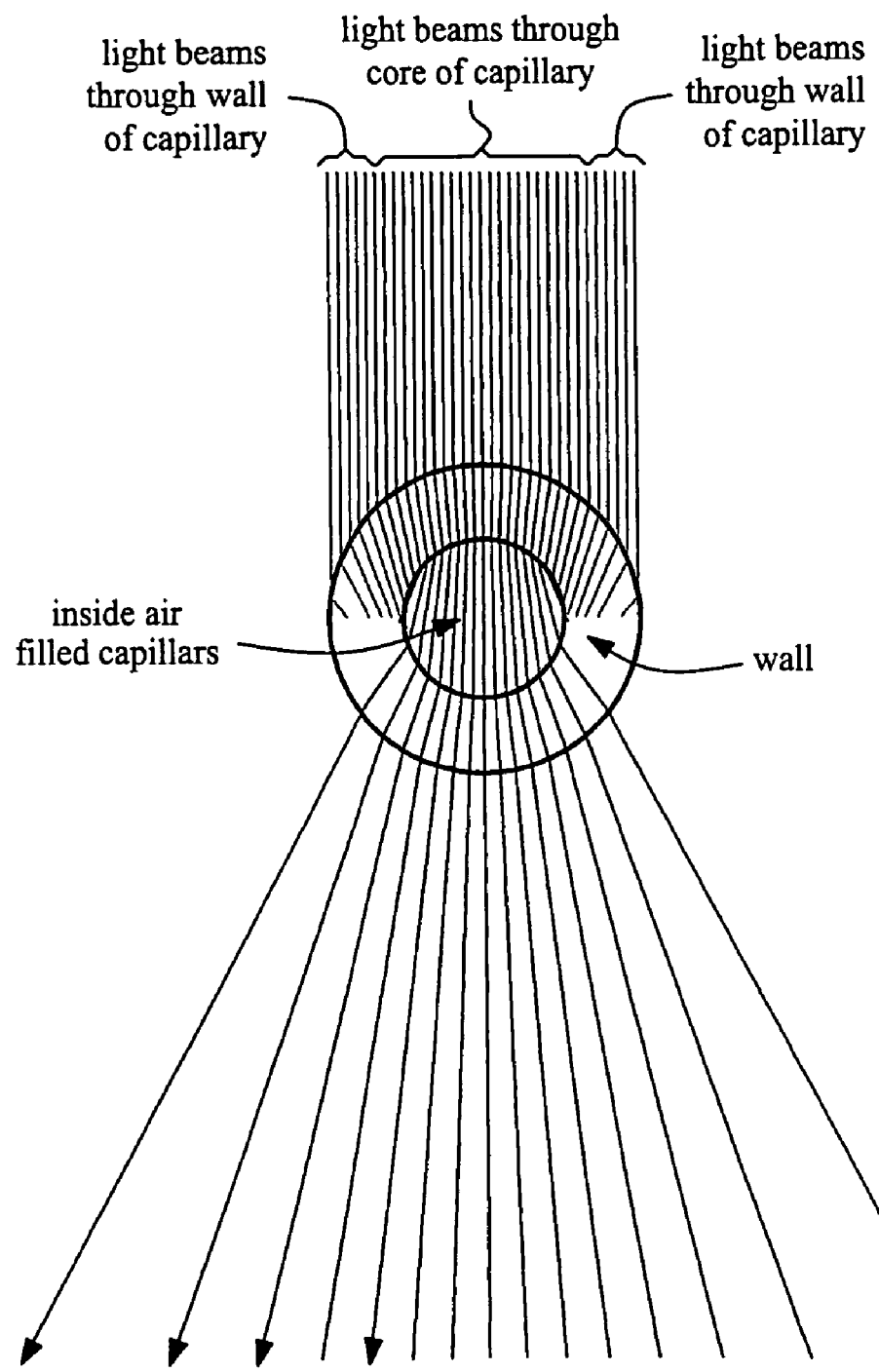
FIG. 6 shows light beam tracings-not-according-to the invention showing light path through an air filled capillary (100 µm i.d., 194 µm o.d.).
Figure 7:
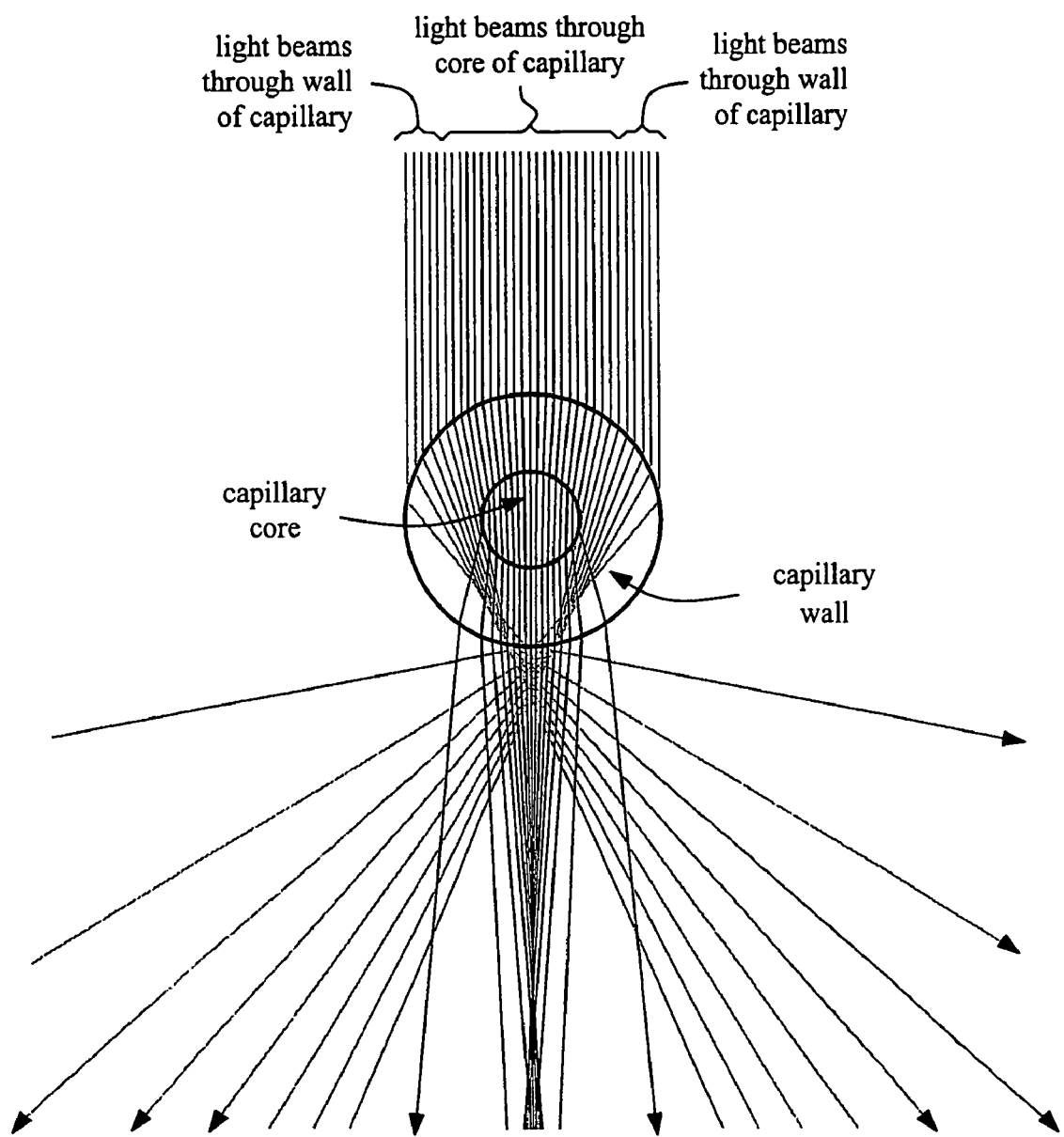
FIG. 7 shows light beam tracings according to the invention showing light path through a water filled capillary (75 µm i.d., 194 µm o.d.).
Figure 8:
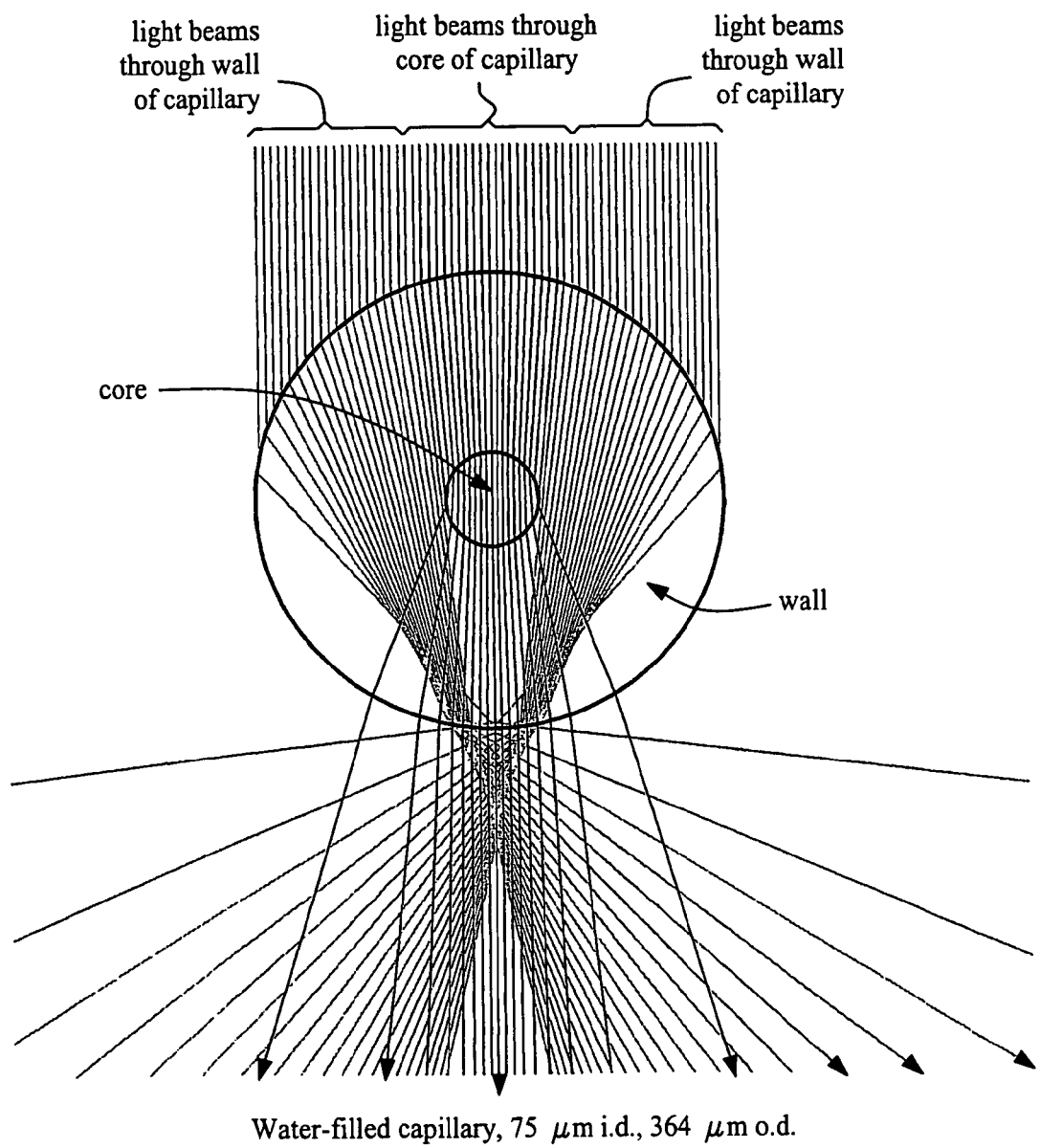
FIG. 8 shows light beam tracings not according to the invention showing a light path through a water filled capillary (75 µm i.d., 364 µm o.d.).

There are situations in which no separation of the core and wall beams is possible. For example, for a cylindrical vessel, this occurs in two generic cases. Firstly, if the refractive index of the material in the core is too low, for example air in a silica or glass vessel (FIG. 6). Secondly, if the ratio i.d./o.d. is too low, for example water in a silica or glass vessel of i.d./o.d. ratio 0.2 (FIG. 8). The actual dimensions for the capillary in FIG. 8 are i.d. 75 µm and o.d. 364 µm, a capillary type widely used in capillary electrophoresis. FIG. 7 shows that for the same i.d. but a smaller o.d., 194 µm, beam separation is readily achieved.

Consideration of the optical properties of filled cylindrical vessels show that the constraints of refractive index and i.d./o.d. are interdependent, emphasizing that for each vessel and contents type, each case should be considered on its merits.

In the case where the refractive index of the vessel contents is higher than that of the vessel walls, no beam separation is possible except at distances unreasonably close to the vessel outer wall.

The vessel may be associated with additional optical components in the emergent light path, to focus or otherwise manipulate one or both of the spatially separated beam types.

Figure 17:
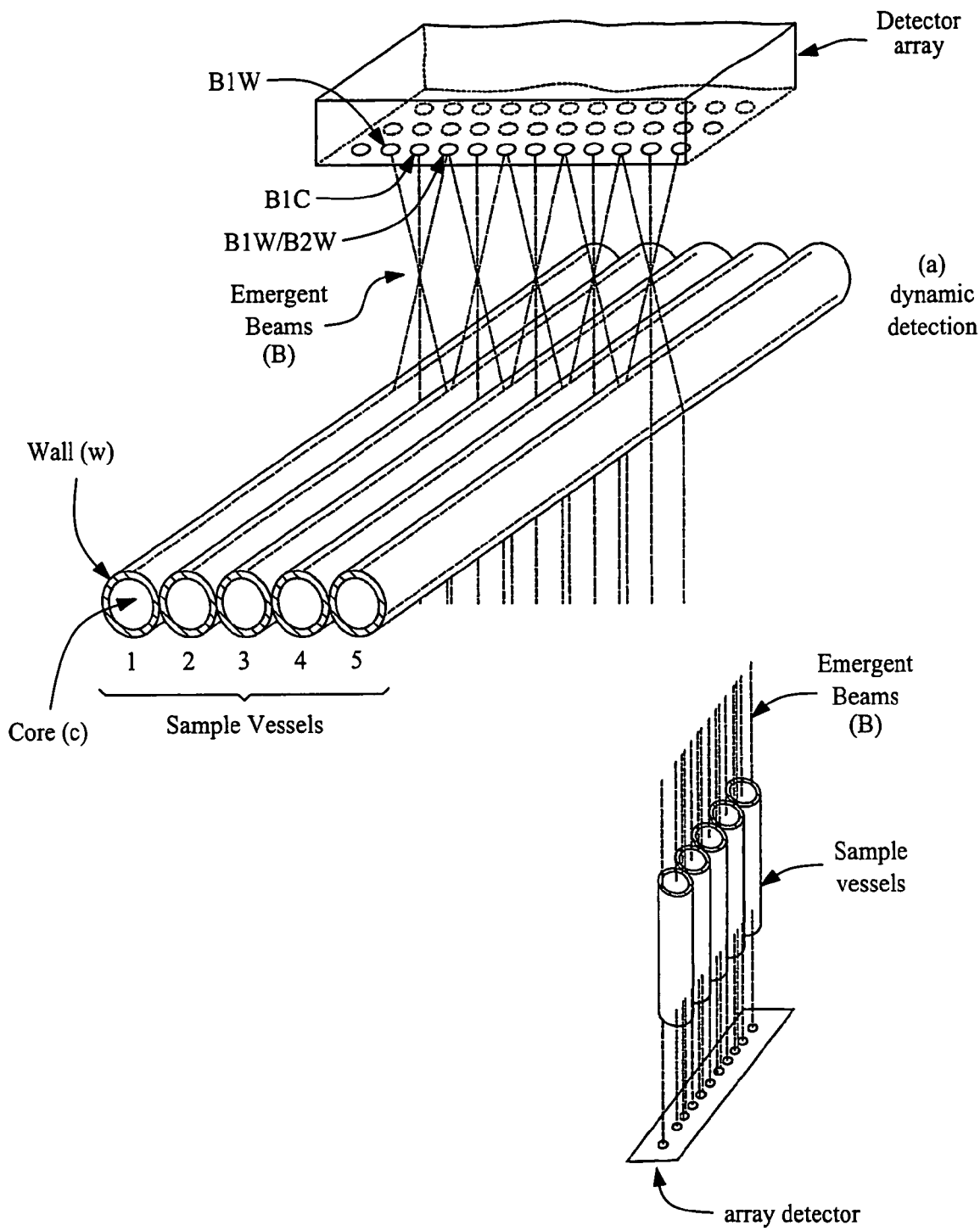
FIG. 17 shows elevations of capillary array type vessels and detection means of an optical assembly of the invention.

The array may comprise fixed or variable spacers between each sample vessel for adjusting spacing of emergent beams B in a sequence for vessels 1 2 3 etc, as shown in FIG. 17, having wall w and core c, for example wherein each beam corresponds to an array detection location:

B1*w* B1*c* B1*w* B2*w* B2*c* B2*w* B3*w* B3*c* B3*w* . . .

If desired, adjacent wall beams may be coincident: B1*w* B1*e* B1*w*/B2*w* B2*c*B2*w*/B3*w* B3*c*B3*w*/ . . .

Other out of step arrangements are possible but may require more complex coupling and reading of detector location.

Spacers may comprise elongate filters designed to screen all or part of a wall light path, or a filter to screen part of the vessel wall thereby confining the wall light paths, in both cases for minimizing intercapillary stray light and cross talk.

A spacer may therefore be of any suitable material for combined spacing and filtration, optionally also serving as support means for the at least one sample vessel, and is of suitable opaque material such as for example an opaque glass filled polymer.

Sample vessels may be comprised of any transparent polymer, glass, quartz, silica, e.g. fused silica or other material, preferably optical grade. Optical grade polymers include the classes of siloxanes such as polydimethylsiloxane (PDMS), amorphous polycycloolefins based on norbornene, and polymethylmethacrylate PMMA, polycarbonate, and other transparent flexible polymers and fluoropolymers. Flexible transparent polymers are commercially available as transparent flexible tubing such as polyetherimide such as Ultem, polypropylene, fluoropolymers including the transparent PCTFE, ECTFE, ETFE, PTFE, PFA, FEP or PVDF resins, preferably the fluoropolymer Tygon chemfluor 367 and the like.

The vessel wall may be transparent in part or whole and is preferably of the same material throughout.

A capillary as hereinbefore defined may comprise any extruded capillary or microfabricated capillary or channel or other parallel elongate closed conduit means. A capillary may be flexible or rigid and may be straight or curved along all or part of its length.

Capillary arrays and microfabricated channel arrays are commercially available. Capillary arrays are typically manufactured by drawing or extrusion, creating a void circular cross-section core of high uniformity dimensions. Microfabricated arrays are typically manufactured by injection molding from a tool, creating a void square or rectangular cross-section channel, which is then optionally sealed with a cover layer, and offers the advantage of absolute reproducibility of highly precise channels, and freedom of channel design.

A sample vessel may comprise part of an array of any number of vessels, commercially available arrays include 8 to 1536 vessels, preferably 8 to 520 capillaries or 96 to 1536 wells, for example 8, 12, 16, 24, 32, 48 or 96 capillaries or 96, 384 or 1536 wells.

The vessel may comprise part of an array of a greater number of vessels which may be available in the future.

Micro fabricated arrays fabricated in layered planar manner, constructing interfacing elements of a device in sequential planes, are gaining acceptance and widespread use. They have numerous advantages in accuracy, reproducibility, ease and flexibility of manufacture.

Vessels may have any desired separation, suitably are fused or adjacent or are spaced apart. A lower separation increases packing density but a higher separation reduces intervessel interference, in particular optical interference. It is a particular advantage of the invention that intervessel spacing may be used. This is not possible in the embodiment of Yeung et al above, for example which needs minimal vessel separation to minimize stray light.

The vessel may be of suitable length and depth according to the desired use. Preferably for capillaries or channels length is in the range 2 cm-2 m for example in the range 2.5-6 cm for microfabricated channels or 6-100 cm length for capillaries, more preferably 10 to 60 cm. Greater length allows application of higher voltage in capillary electrophoresis and improved separation. For microtitre plate well, preferable inter-vessel center to center spacings are compatible with standard microtitre plate formats, such as 2.25, 4.5 and 9 mm.

Preferably a vessel is of 3 μm to 20 mm in depth or internal diameter, and 4 μm to 30 mm in external diameter, more preferably 9 μm-3 mm in depth or internal diameter and 10 μm to 3.5 mm in external diameter, more preferably 10-380 μm, most preferably less than or equal to 200 μm in depth or internal diameter or external diameter. A vessel wall is importantly of suitable thickness for the optical properties of the invention. This is particularly relevant for vessels of small internal diameters. Accordingly vessel internal diameter or "bore" may be selected and vessel wall material selected, and suitable outer diameter determined accordingly to give the required optical properties. For silica capillaries with internal diameter (hereinafter i.d.) in the range 20 to 250 μm, for example 20, 25, 50, 75 or 100 μm, external diameters (hereinafter o.d.) is preferably in the range 100 to 380 µm, for example 150, 200 or 360 µm. For example a vessel may be of 75-100 µm i.d. and 194 µm o.d. or 180 µm i.d. and 364 µm o.d. It is important to note that for a vessel with 75 µm i.d. and 364 µm o.d., as widely used in capillary electrophoresis, no separation of core and wall beams is possible when working with aqueous solutions. For silica capillaries, thickness is suitably in the range 30-500 µm, for example 30-150 µm: vessels of low i.d. preferably have low wall thickness, to give a minimum i.d. to o.d. ratio of 2-4 for example 0.25.

When working with larger diameter reaction vessels, similar constraints apply, but normally the i.d./o.d. ratio falls in the range giving suitable beam separation. For example, a glass reaction vessel having an i.d. of 20 mm and an o.d. of 30 mm has an i.d./o.d. ratio equal to 0.67, which permits beam separation with all common solvents (see Table 1). For a polycarbonate reaction vessel and water as solvent, for an i.d. of 0.33 cm, an o.d. of 1.0 cm would be suitable, but an o.d. of 1.5 cm would be unsuitable. For a representative fluoropolymer tubing, Tygon chemfluor 367, with i.d. 1/16" (1.6 mm) and o.d. 1/8" (3.2 mm), the i.d./o.d. ratio is 0.50 and beam separation with solvent water is achieved for all values of the ratio d/o.d. greater than 0.4, i.e. d>1/20" (1.3 mm). However, when working with hexane as a solvent in such tubing, the refractive index of the vessel contents is greater than that of the walls (values of refractive indices are given in footnote to Table 1), and no beam separation is possible other than at distances unreasonably close to the vessel outer wall.

The sample vessel may be void or packed, for example may comprise stationary phase or may be coated or otherwise configured with suitable materials as known in the art for example in HPLC. Suitably packing if present is of corresponding refractive index to bulk phase sample or to solvent comprised in sample to be detected.

Preferably the vessel comprises internals and components characteristic of columns or capillaries present in pressure driven or electrical driven separations including HPLC (for pressure driven) or capillary electrochromatography (CEC) (electrically driven equivalent of HPLC, separating by binding or partition coefficient, using eg hydrophobic stationary phases), micellar electrokinetic chromatography, and capillary electrophoresis (CE) including the focusing and concentrating techniques of isoelectric focusing (IEF separating by isoelectric point independent of size and shape of molecules), isotachophoresis (ITP), capillary zone electrophoresis (CZE separating by charge to size ratio) and dynamic field gradient focusing (DFGF, where a constant hydrodynamic force is opposed by a gradient in the electric field, which allows charged molecules to focus in order of their apparent electrophoretic mobilities and selective concentration of analytes e.g. proteins—see "Digitally controlled electrophoretic focusing" Huang and Cornelius, Anal. Chem., 1999, 71, 1628-1632).

The separation between a sample vessel and the detector, d, is suitably such as to facilitate coupling of spatially separated light paths to the detector locations. Suitably the separation is a function of the vessel o.d. and of the degree of separation of light paths, and is preferably given by the ratio d/o.d. is less than 10, for example is in the range 0.5-5, preferably 0.5-1. In a particular advantage the optical assembly of the invention allows an extremely compact structure when working with capillaries in which separation d is of the order of 50-360 µm, for example 200 µm. This is particularly advantageous since the lesser the value d the more compact and robust is the assembly and the more intense are the transmitted light beams at the detector. The separation d may be adapted to couple spatially separated light paths in sequence as hereinbefore defined, with or without intervening optical components and preferably without intervening optical components.

There are a number of commercially available array detecting systems, including for example the commonly used photodiodes and more recently available charge coupled devices (CCDs) and active pixel sensors (APSs) eg complementary metal oxide semiconductor (CMOS). Preferably therefore an array detector according to the invention comprises a solid state sensing device, more preferably a CCD, CID or a CMOS APS.

A detection zone may be of any desired area size and is suitably of zone dimensions substantially equal to the vessel or array cross section in a plane perpendicular to the light path, corresponding to one to one image. A detection zone may comprise one or a plurality of array detectors.

Smaller zone size increases noise and reduces sensitivity yet can be provided at lower cost. Preferably the apparatus comprises lowest noise and highest sensitivity CCDs in a relatively small area device, such as a 1024×256 pixel CCD (MAT CCD30-11).

A CCD for use in the apparatus of the invention may have 22 to 5000 or more pixels in either dimension, preferably 256, 512, 770, 1152, 2048 or 4096 pixels, of pixel size 7 to 35 µm, preferably 20 to 30 µm, more preferably 22 to 30 µm. Preferably the CCD comprises 3 to 28, for example 10 pixels per capillary or 30 to 2500 for example 100 pixels per well. Pixels outside the imaging area are preferably not digitized to reduce readout time.

Commercially available CCDs may include a stud, for protection of the CCD surface which is usually recessed in the CCD support package and to conserve image quality. Preferably the stud comprises a coating to absorb incident light and reemit at a different wavelength, to convert UV to visible light, to allow detection by the CCD. A coating is for example a phosphor coating. The phosphor coating may be applied directly to the stud or to a cover slip interleaved between the stud and capillary, facilitating changing phosphor as needed, by replacing the cover slip without need to replace the stud.

Each camera is interfaced to control means, preferably a processing control means providing a suitable pixel readout rate, suitably of the order of MHz, preferably greater than 4 or 5 MHz.

Preferably the processing means is programmed for selection of on-chip charge binning procedures, to increase signal current (photoelectrons per second) and selection of area of interest for read out. Additionally the processing means controls camera readout and collects, stores and analyses data.

In the case of an assembly comprising a conduit sample vessel intended for dynamic sample detection, preferably the apparatus operates with real-time signal processing for optimum peak detection and parameterization/characterization, and potential for automatic system management including closed-loop feedback control of the apparatus and systems. For example, feedback could include stopping or slowing the flow following initial observation in the detection window, to allow sample to reside in the detector window and give longer times for data acquisition and enhanced signal to noise or to facilitate detection along the length of a vessel.

Flow velocity may be controlled by adjustment of electric field (as in capillary electrophoresis) or by adjustment of pressure (as in liquid chromatography), or by a combination of the two. For flow driven by centrifugal forces, flow velocity control is carried out by adjustment of the angular velocity.

Figure 13:
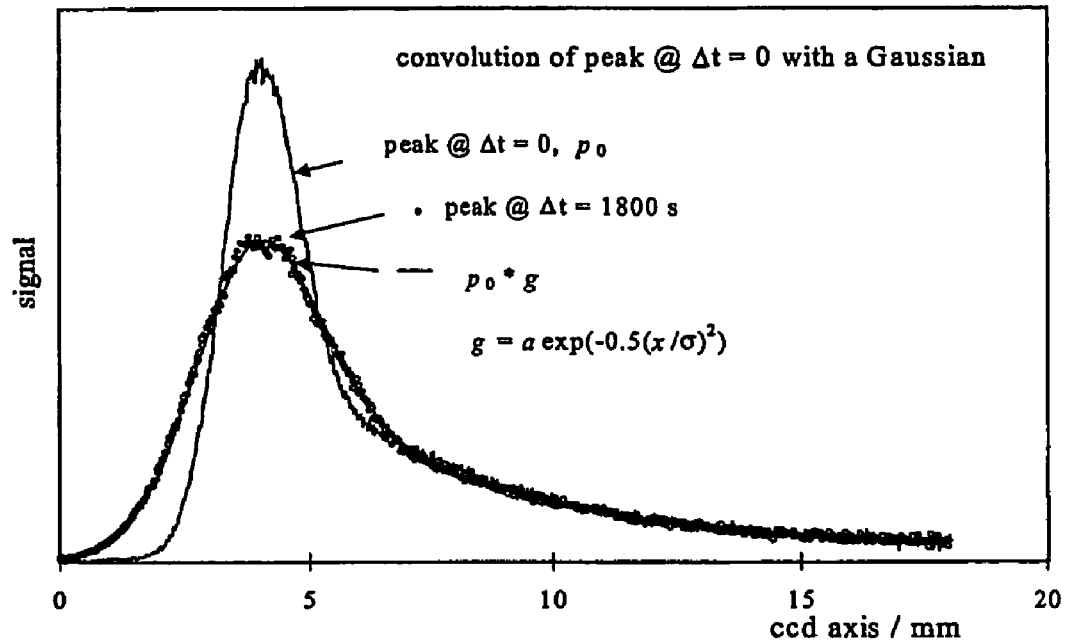
FIG. 13 shows peak imaging and variance for a sample of rhodamine 700 injected onto a capillary and migrated by CE to the detection zone which is imaged by laser induced fluorescence with a CCD. The voltage is turned off (at delta t=0) and the peak broadening due to diffusion is monitored for 1800 s (top). The change in peak variance is plotted against time (bottom).
Figure 13:
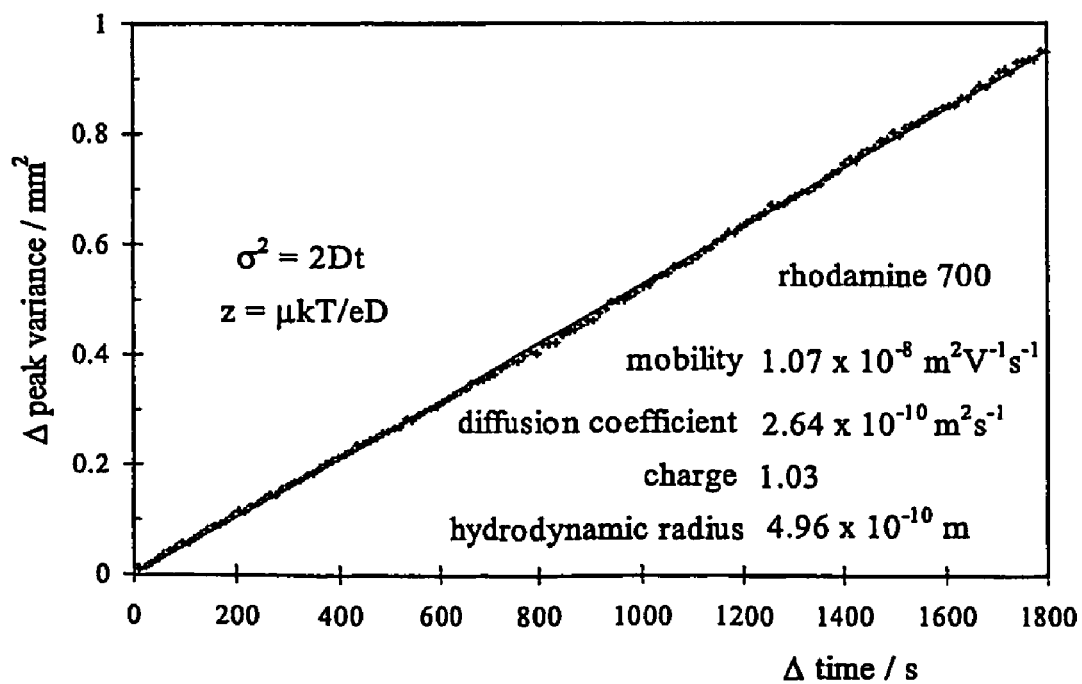

Suitably the assembly comprises means to detect presence of sample in a detection window, and feedback control means for turning off the voltage when it is detected as having migrated to the center of the window (see FIG. 13). Feedback control means suitably includes means for monitoring the subsequent broadening of the sample peak due to diffusion as a function of time, and for analysis of the change in peak variance with time, and determining the diffusion coefficient, enabling the hydrodynamic radius of the analyte to be deduced, and means for combining with the mobility, obtained from the time taken to reach the window under a given field strength, enabling the charge on the analyte to be deduced. The control means is able to operate with any starting peak shape, since convolution of the peak with a Gaussian enables the Gaussian component of the peak broadening to be extracted. Data quality obtained with the assembly of the invention is such that diffusion coefficients could be measured with good precision in less than 3 minutes. This assembly could be used to measure diffusion coefficients, size and charges of both small molecules and large molecules, including proteins, DNA, and polysaccharides, and offer a simpler alternative to analytical ultracentrifuge methods.

Alternatively closed loop feedback could include means such as peak recognition and decision making software for instructing a switching valve and controlling switching times to enable fraction collection, or to direct a fraction to a mass spectrometer, e.g. via an electrospray interface, or to a NMR spectrometer. Means for observing the flow stream both before and after the valve enables the quality of analyte switching and efficiency of the switching means to be monitored. A schematic example of closed-loop feedback control is given in FIG. 14. Preferably the assembly positions the capillary in two separate light paths and to generate two sets of spatially separated transmitted light paths coupled to two detectors or detector zones with the switching valve therebetween whereby after the appropriate switch the eluent is monitored again in a second pass of the detector, so that the efficiency of the switching process can be monitored. An alternative is to have more of the outputs of the switching valve passing the detector for visualization.

Closed loop feedback may also include controlling velocity of samples in multiple vessels, for example in a capillary array, to co-ordinate exit times, in sequence or, for combining samples from different capillaries into a common exit means, simultaneously. Velocity may be controlled by controlling voltage or pressure, for example pumping flow rate, and may be operated with switching devices. Velocity may enable stopping samples flow at desired time to coincide with an event which is to be performed on the sample or is to take place in the sample. Controlled exit may be for subsequent fraction collection or analysis, for example for interfacing the output of a capillary bundle to a mass spectrometer by electro-spray, or to an NMR spectrometer or the like.

Preferably controlled loop feedback is provided by creating a potential difference across the length of the capillary and/or varying the applied voltage to control migration of sample, including slowing or stopping to improve signal/noise ratio and including timing sample migration to achieve a desired time of arrival of sample at a point to switch into a sample collection means such as mass spectrometer. The system may operate with a pressure difference and pumping, electrical field driver, column switching or the like. Preferably therefore a capillary comprises electrodes, valves or pressure regulators at the ends thereof or along the length thereof about the detection zone or each detection zone together with circuitry to control electrodes or to facilitate pumping control. In the case of voltage controlled migration, preferably a sample vessel is connected to a buffer supply and electric field is arranged such that buffer supply and sample introduction is at the high potential end of the capillary, where high may be either positive or negative with respect to ground.

In a further aspect of the invention there is provided an optical assembly module for use with a column or capillary separating device as known in the art, wherein the vessel is a capillary or column comprising interfacing means at one end for inserting into the outlet of a column or capillary separating device and optionally comprising interfacing means enabling insertion into the inlet of an analyzing means at the other end or comprising interface means at both ends for insertion along the length of a capillary or column. A module for insertion along the length of a column or capillary typically has a column or capillary section of matching i.d and o.d as the separating device or interfacing means allowing a smooth flow transition.

In a further aspect of the invention there is provided an optical assembly clip-on device adapted to locate about a section of a capillary or column which is of suitable i.d, o.d and refractive index as hereinbefore defined comprising means to locate about the capillary or column of a separation device. Optionally the capillary or column has its outlet inserted into the mass spectrometer, in which case the clip-on is located as close to the mass spectrometer as possible. In the case of a clip-on, the capillary or column of the separation device may be stripped of any surface coating to facilitate the operation of the method of the invention, whereby the stripped capillary or column, such as a capillary electrophoresis or microbore HPLC section, provides the sample vessel of the assembly.

In a further aspect of the invention there is provided an apparatus for chemical reaction or synthesis and analysis or for sample separation or transport wherein the apparatus comprises the optical assembly as hereinbefore defined. The chemical reaction vessel itself could be cylindrical and the reaction monitored in batch flow mode as a function of time, and feedback control used to halt reaction—e.g by admixture of a quenching reagent, by change of temperature, or by exporting the vessel contents. Alternatively the reaction vessel could be tubular and used in continuous flow mode. The apparatus may comprise a plurality of means for introducing one or more reagents to the at least one sample vessel together with means for regulating reaction conditions to form a desired chemical synthetic reaction within the at least one sample vessel; or may include means for inlet and outlet of sample in dynamic fashion into the at least one sample vessel together with means for applying a pressure difference or potential difference across the ends of the vessel and means for supplying separation mediums such as buffer in order to perform separations within the at least one sample vessels: or may include a separation means such as a chromatography column as known in the art having outlet interfaced with an inlet end of the at least one sample vessel as hereinbefore defined for dynamic analysis of separated sample.

In a further aspect of the invention there is provided a method for detection of light transmitted through at least one sample contained within the core of at least one sample vessel of an optical assembly as hereinbefore defined, comprising illuminating the vessel with a substantially collimated light source or sources and detecting transmitted light in a detector, wherein transmitted light is spatially separated into at least two light paths, a wall path which has passed through the vessel walls only, spatially separated from a core path which has passed through the walls and core, wherein the spatially separated light beams are coupled to individual detection locations on the array detector. Suitably the method comprises any features or embodiments corresponding to apparatus features and embodiments outlined above.

Preferably the method is a method for detecting light from samples in sample analysis for example for high throughput screening (HTS) or profiling or assays, such as enzyme assays; and uses thereof in the pharmaceutical, biomedical and bioscience, healthcare, agrochemical, veterinary, industrial, environmental or materials or like fields, for detection, analysis, characterization and quantification or the like of samples contained in a vessel, and optionally further collecting separated components thereof; in particular in combinatorial chemistry; in metabolomics, proteomics or genomics, assay and high throughput analysis applications, typically high sensitivity analyses, separation and/or quantification studies and for sample separation for example chromatography or electrophoresis, in particular column chromatography, capillary electrophoresis with real time or post separation analysis, in hospital or surgery blood tests and other assays, in industrial quality control, in environmental pesticide level monitoring and the like.

The method may be a method for detecting light from a static or dynamic sample. Typically a static sample is contained in a closed ended sample vessel as hereinbefore defined, more typically in a vessel in the form of a cell or well which may be one of a plurality of vessels for example in a microtitre plate or a well plate or sample plate as hereinbefore defined. Samples derived from enzyme assay or other multiple sample analysis may be in this form for detection.

In one embodiment the method is a method for single capillary or multicapillary absorbance detection, comprising drawing solvent then sample into the capillary(s), by capillary action, pressure, pipetting or the like, conducting detection of difference in transmittance of sample and solvent, and disposing of or blowing sample back to the source. This method is useful in bioscience for making absorbance measurements on small sample volumes of microlitres or less. Enzyme assays may be conducted with one or two streams entering the vessel and detecting a time dependent change, normally in profiling, for enzyme assay.

Typically dynamic samples are electrically or pressure driven and are present in an open ended conduit type vessel as hereinbefore defined, such as a capillary having inlet and outlet ends for flow of sample through the capillary, the capillary may be a single capillary or part of a capillary array as hereinbefore defined. Samples derived from high throughput screening or from the separation or transport techniques may be provided in this manner for detection, of which samples derived from separation techniques may be provided for separation within the capillary with simultaneous detection of light transmission, or may be separated in a separation method such as column chromatography, and the separated sample flow from the column coupled directly into a capillary for detection of light transmission.

Preferably the method for detecting a dynamic sample is a method for column or capillary separation as known in the art, suitably selected from pressure driven or electrical driven separations including HPLC (for pressure driven) or capillary electrochromatography (CEC) (electrically driven equivalent of HPLC, separating by binding or partition coefficient, using eg hydrophobic stationary phases), micellar electrokinetic chromatography, and capillary electrophoresis (CE) including the focusing and concentrating techniques of isoelectric focusing (IEF separating by isoelectric point independent of size and shape of molecules), isotachophoresis (ITP), capillary zone electrophoresis (CZE separating by charge to size ratio) and dynamic field gradient focusing (DFGF, where a constant hydrodynamic force is opposed by a gradient in the electric field, which allows charged molecules to focus in order of their apparent electrophoretic mobilities and selective concentration of analytes e.g. proteins—see "Digitally controlled electrophoretic focusing" Huang and Cornelius, Anal. Chem., 1999, 71, 1628-1632). Other electrically driven techniques are known or may be developed in future.

A method which is a method for electrophoretic separation of molecules is carried out with an assembly, module or clip-on in a capillary or channel as hereinbefore defined which is connected to a buffer supply. An electric field in the range of kilovolts is applied across both ends of the capillary or channel to cause the molecules to migrate. Samples are typically introduced at a high potential end and, under the influence of the electric field, move toward a low potential end of the channel. Absorbance analysis may be conducted along the length of the capillary or channel or near the outlet allowing observing an entire process taking place in the length of the capillary or channel or the result thereof.

Another use of dynamic detection is in measuring refractive index change. By analysis of the illumination pattern of the core beam at high spatial resolution perpendicular to the capillary axis, the detector has the ability to monitor refractive index change in the solvent in the capillary. This would allow distinction between two solvents, and by extension the ability to directly monitor the mobile phase composition during a gradient elution separation in dual solvent mixtures. If necessary, magnification in the direction perpendicular to the capillary axis could be used to increase the resolution in terms of mobile phase composition. This would be of benefit in HPLC. Since solvent refractive index may be temperature dependent, application of a heat pulse providing a temperature rise up-stream of the detector could be used to determine the mobile phase velocity in capillary HPLC.

Another use of multicapillary absorbance detection is for rapid measurement of $pK_a$. Here aliquots of the sample solution are mixed into a set of buffer solutions covering a range of pH values, typically spanning the range 2-12, and all mixtures are then drawn up into separate capillaries in the sequence buffer then mixture of buffer plus sample. By taking measurements at one or more wavelengths where acid and base forms have different absorbance, results from all capillaries of absorbance as a function of pH may be processed to determine $pK_a$ values. Using suitable non- or weakly-absorbing inorganic buffers, this is applicable for organic or biological compounds containing all common titratable functional groups, including carboxyl and amine groups, and at concentrations down to 100 micromolar. This is of benefit in for example the pharmaceutical industry and for high throughput screening.

The invention has particular use in relation to samples of small molecules of MW of the order 15-500, but may also be used in relation to samples of larger molecules such as polymers, proteins, DNA and other biomolecules of MW of the order 500 to $10^6$. The invention is of particular advantage in one embodiment due to its small size. This may be employed to advantage in hospitals and the like for sample analysis, without the need for clinical biochemical laboratories, for example as a color assay. Blood tests may be conducted on blood samples which are currently spun to separate red blood cells and plasma in a laboratory. The assembly of the invention may be used to detect red blood and plasma, either before or after centrifugation, for example by adding a reagent to the plasma region and observing the reaction.

In an alternative embodiment multiple wavelength detection allows detection at a range of wavelengths along the length of a capillary or channel.

Preferably the method is a method enabling or allowing some transformation or event to occur in a vessel and imaging the event. Imaging may be conducted at the end of the transformation or event or throughout. Imaging throughout an event requires timing to coincide with migration of sample in the vessel, preferably using controlled loop feedback as hereinbefore defined to stop the sample migration in the vessel at desired location or interval for imaging.

For example the method may be a method for observing a chemical reaction for biomedical, bioscience, healthcare, agrochemical, veterinary, pharmaceutical, industrial or environmental purpose, wherein multiple detection may be performed on the inlet and outlet and in the waste to ensure that all of the reaction product has been collected. The reaction may be conducted in the vessel in the form of capillary which may be curved, allowing ease of detection of multiple positions using a common light source and detector.

In an alternative embodiment the method comprises detecting sample from pharmaceutical studies, in the form of analyte in solvent such as dimethylsulfoxide (DMSO), stored in microtitre plates, as is common in pharmaceutical practice. The method of the invention may be performed on samples either in the microplate array in situ, as a vessel array as hereinbefore defined or following drawing up portions into one or more capillaries, as a single capillary or capillary array. Use of a short path length of less than 9 mm, preferably of the order of 300 µm or less, allows UV absorbance detection without total absorption of light by the DMSO solvent.

In an alternative embodiment the method is a method for measuring physico-chemical properties for example partition coefficients, comprising placing sample of analyte in a first solvent in the vessel, together with a second immiscible solvent, for example water and octanol respectively, and observing the analyte moving between the two immiscible phases. In a particular advantage the method of the invention also enables imaging of the solvent phases whereby their interface is also visible.

In an alternative embodiment the method may be a method for detection of light from a plurality of sample vessels for high throughput analysis of different samples in each vessel, for example for comparative analysis thereof or may be a high loading method for detecting in each vessel the same samples from a high volume, high flow or otherwise bulk upstream process, intended for combining a desired component from each sample. A high loading method may comprise introducing the output from a single HPLC for example having flow rate exceeding that possible in a single capillary, but suitable for introducing into a capillary array which may then function effectively as a single detector. For example the method may comprise detecting analytes present in sample in or exiting a microbore liquid chromatography column and the column may be of diameter in the micron range up to millimeter range. High loading in a plurality or array of vessels achieves higher resolution in separation and potentially higher sensitivity in detection than operation on a large scale in a single vessel from a single large bore separation channel. Moreover a shorter path length is possible in an array of capillaries than is possible in a standard HPLC cell and this allows operation at a lower wavelength as hereinbefore defined.

A method for detection in DFGF or multiple detection method preferably employs feedback control as hereinbefore defined.

Preferably the method comprises illuminating the at least one sample vessel with collimated light comprising a single or a plurality of wavelengths selected in the range as hereinbefore defined. In a particular advantage illumination is with a collimated light source of a single wavelength at any given time, thereby simplifying readout of optical detection results.

A sample as hereinbefore defined may comprise any sample of one or more small or large molecules present in liquid or gel phase suitably in solution with liquid phase solvent or cosolvent such as an inert or non reactive liquid. Solvent or gel may have refractive index in the range as hereinbefore defined. Suitably however these samples are characterized by a refractive index of lower than but of similar order to that of the sample vessel walls, whereby the sample provides a generally convergent light path. Preferably therefore the sample comprises a solution or a suspension of molecules to be detected in a solution or suspending medium selected from water, alcohols, acetonitrile, hexane, dichloromethane, acetone, DMSO and other common solvents and cosolvents and mixtures thereof; or the sample may be provided in the form of a gel for example uncrosslinked polymer solutions such as cellulose derivatives (e.g. hydroxypropyl cellulose) and synthetic polymers (e.g. polyethylene oxide).

Preferably the method of the invention comprises selecting a sample for analysis, determining individual wavelengths at which absorption by desired sample components is strongest, checking refractive index of the sample in order to select a suitable sample vessel which when containing the sample and when illuminated will generate spatially separated beams as hereinbefore defined or selecting a suitable combination of optical components, filters and the like and a suitable vessel to detect an array separation to couple spatially separated beams to independent locations on the detector array.

Sample may be introduced into the at least one sample vessel as hereinbefore defined in known manner, for example by injection, loop injection, pipette, hydrostatic, electrokinetic or like injection techniques and may be removed from the vessel in known manner such as injection, electrospray or other interface for discard or to a further vessel for storage or to a down stream identification means such as mass spectrometer.

Detected light is coupled to individual detection locations on the array detector as hereinbefore defined. The at least one sample vessel as hereinbefore defined is coupled to a plurality of detector locations in manner that core detector locations correspond to the core light path from the at least one vessel and peripheral detector locations correspond to the peripheral wall point(s) from the vessel. Preferably the method comprises imaging the transmitted light detected by the detection means, for example in the form of a CCD image as known in the art. Preferably the method also comprises referencing the light detected by the detection means by means of exposure referencing wherein the ratio of the core beam intensity to the wall beam intensity gives a value for the sample intensity at each location with elimination of excess or flicker noise due to light source fluctuation.

Accordingly therefore the method comprises coupling the at least one sample vessel to at least three detector locations, preferably 3 to 25 detector locations for a sample vessel of the order of microns diameter wherein the locations may be apportioned for example 1:1:1-5:15:5 or 8:9:8 depending on the relative wall and core beam width; and for a sample vessel of the order of cm in an amount of 30 to 2500 pixels per sample vessel for example in the ratio 5:20:5 or 10:10:10 to 500:1500:500 or 800:900:800 depending on the relative wall and core beam width. The method may include pixel summing or the like for enhanced signal strength and noise reduction as known in the art.

Preferably the method includes subsequently measuring the amount of absorption of light by species in the sample vessel which indicates the amount of absorbing species in manner as known in the art and comprising measuring the intensity of light in the absence and presence of the sample. In a particular advantage measurement according to the invention is simply by measuring intensity of light in a wall beam and a core beam. The logarithm of the ratio, taken in conjunction with values measured in the absence of sample, provides the absorbance according to the Beer-Lambert Law.

Absorbance may be imaged, for example as a CCD snapshot. Preferably however the method is a method for snapshot detection whereby detection is recorded in a plurality of finite exposures, for example five exposures per second, and exposures are super imposed, directly in the case of a static example or with time displacement in the case of a dynamic sample. Accordingly an individual image reveals limited information and therefore the detection array preferably provides raw data which is compiled and converted to graphical display for example in the form of an electropherogram.

In a further aspect of the invention there is provided the use of the optical assembly, method and apparatus as hereinbefore defined in sample analysis for example for high throughput screening (HTS), for example in an array as hereinbefore defined, or profiling or assays, such as enzyme assays; and uses thereof in the pharmaceutical, biomedical and bioscience, healthcare, agrochemical, veterinary, materials, industrial, environmental, and like fields, for detection, analysis, characterization and quantification or the like of samples contained in a vessel, and optionally further collecting separated components thereof; in particular in combinatorial chemistry; in metabolomics, proteomics or genomics, assay and high throughput analysis applications, typically high sensitivity analyses, separation and/or quantification studies and for sample separation for example chromatography or electrophoresis, in particular column chromatography, capillary electrophoresis with real time or post separation analysis; in hospital or surgery blood tests and other assays, in industrial quality control, in environmental pesticide level monitoring and the like.

The invention is now illustrated in non limiting manner with respect to the following examples.

EXAMPLE 1

Figure 2:
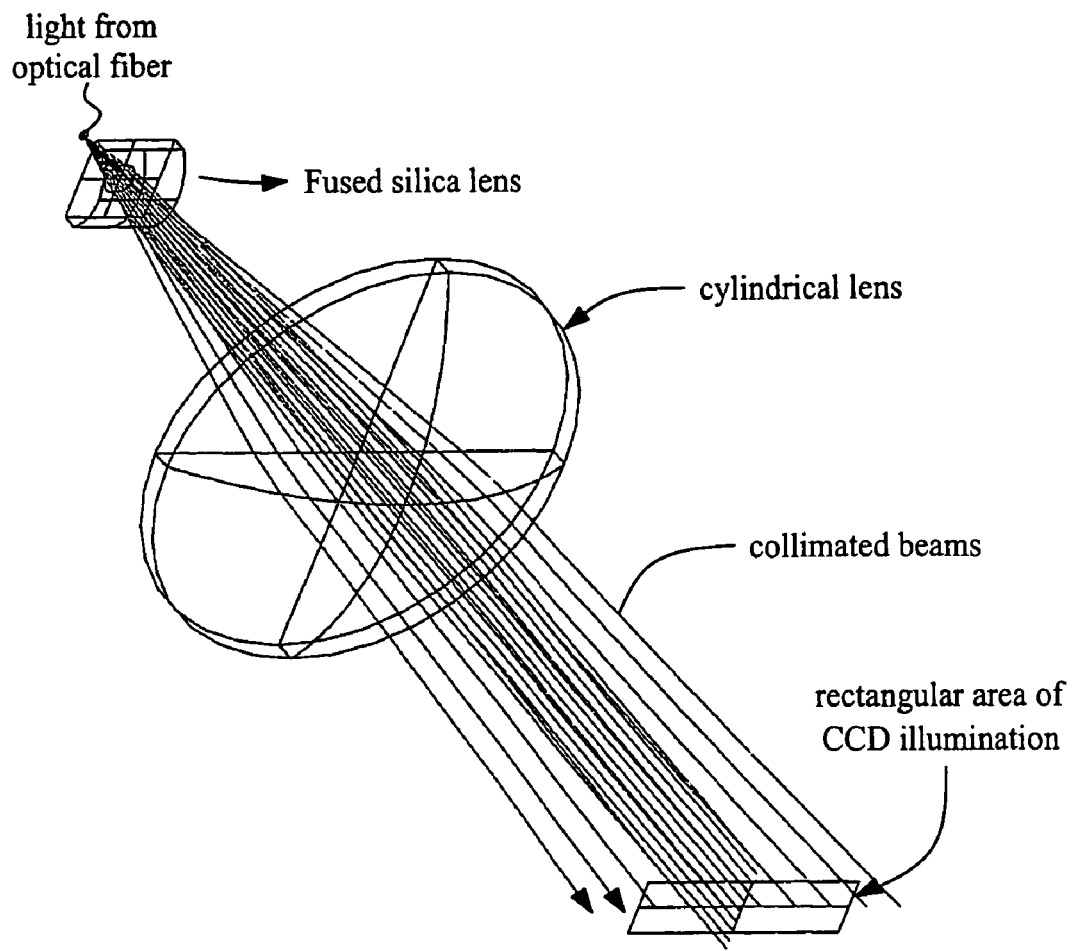
FIG. 2 shows a collimated illumination of rectangular CCD area (26.6×6.7 mm) using light output from a 1 mm diameter fused-silica optical fiber (N. A. =0. 22) using a cylindrical and spherical fused-silica lens element.

The experimental setup is shown in FIG. 1. The output from a 75 W xenon lamp is launched into a single 1 mm diameter fused silica fiber. The light output from the fiber is shaped and collimated using cylindrical and spherical fused silica lens elements (FIG. 2) to illuminate the rectangular area of the CCD. The CCD chip used is EEV CCD 30-11 and is thermostatted and controlled by a system designed and built by York Electronics Center; it has 1024 by 256 active pixels, each 26 µm square, with a total active area of 6.7×26.6 mm. The CCD chip has a fiber optic stud (faceplate) that protects the CCD surface. The fiber optic stud is not UV transparent, so a UV phosphor is coated onto the surface of stud to make the detector sensitive to a wide wavelength range from NIR to below 200 nm. The charge accumulated on the CCD is read out in a series of snapshots; to prevent image smearing a light chopper ensures that the CCD is not illuminated during the readout period. An exposure rate of 5 Hz is used with a 50% duty cycle (100 ms exposure and 100 ms readout time). An image of 1024×256 pixels with 14 bit digitization is obtained from each snapshot.

An ideal arrangement of the capillaries could be to align them parallel to the short axis of the CCD at a spacing of 260 µm (10 pixels per capillary). This arrangement would allow up to 102 capillaries, which is ideal to accommodate the number used if sampling from a standard 96 well plate. The spacing means a gap of 66 µm between each capillary, this would allow more reference light reaching the CCD than in the current arrangement with the capillaries more tightly packed. Better exposure referencing and lower inter capillary cross talk should result from this arrangement.

Capillary Imaging

Figure 3:
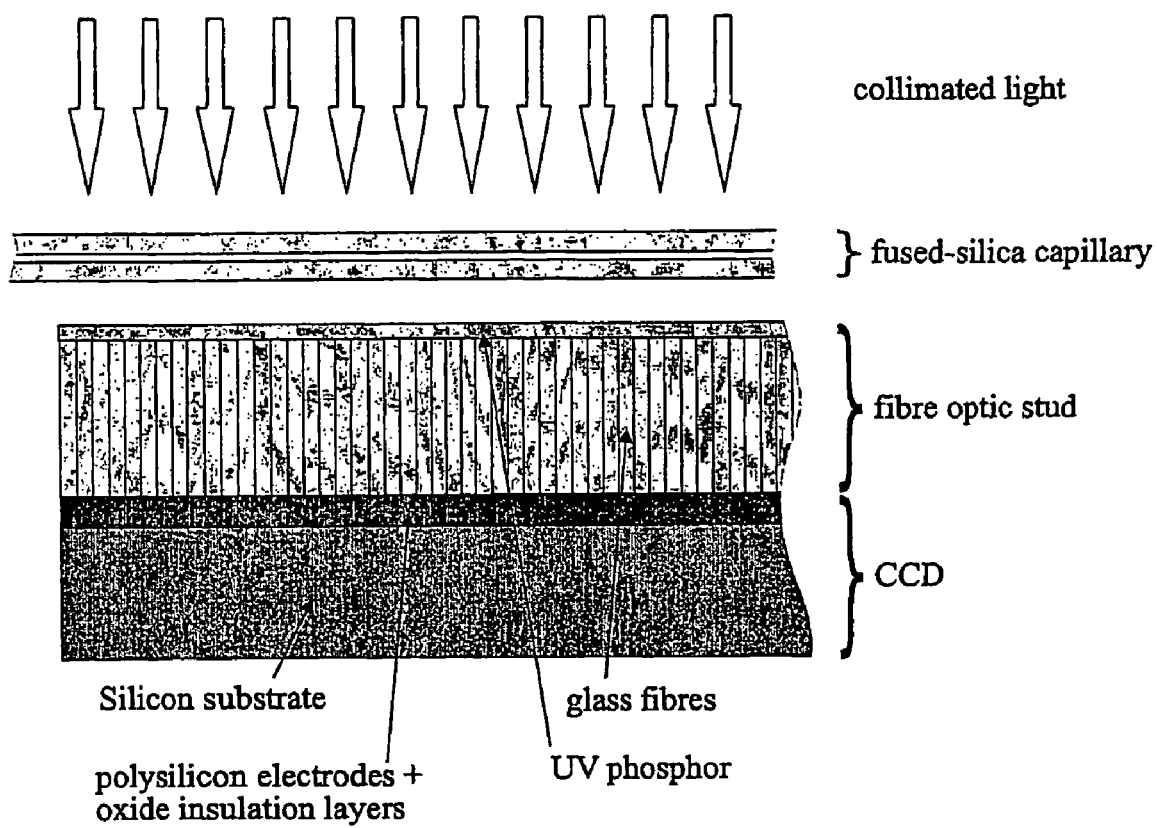
FIG. 3 shows the CCD and vessel arrangement of the optical assembly of the invention.
Figure 4:
FIG. 4 shows part of one CCD snapshot showing ~3 mm of 4 capillaries (100 µm i.d., 194 µm o.d.); the total area imaged is 6.7×26.6 mm. The contents of the capillaries are: 1) Air, 2) Water, 3) and 4) ink solution.

In the demonstration experiment four fused silica capillaries (100 µm i.d., 194 µm o.d. 500 mm long) were placed side by side, approximately 200 µm above the CCD and parallel to the long axis of the CCD as shown in FIGS. 1 and 3. The portion of the capillaries imaged was a section 273.4 to 300.0 mm from the inlet end. FIG. 4 shows a portion of one snapshot taken with the four capillaries filled with air, water and the last two with an ink solution. Excellent referencing is seen for the assembly without any lenses or other optics. It can be seen from the comparison between capillaries 1 and 2 that the collimated light that passes through the capillary core is convergent when the capillary is filled with water, producing a line that is brighter than the background. FIGS. 5 and 6 show in detail how light passes through the water and air filled capillaries; they show also that in the case of the filled capillary, there is good separation on the CCD between the light passing through the capillary core and that only passing through the capillary walls. This is confirmed in FIG. 4 where a high contrast is observed between the images of the water and ink filled capillaries. It is important to use capillaries with a small o.d.; FIG. 7 shows that good results would be obtained using capillaries with the same o.d. of 194 µm as used here but with the more commonly used 75 µm i.d. However, the 364 µm o.d. capillary normally used in capillary electrophoresis would not be suitable; FIG. 8 shows that the larger radius at the air/fused-silica interface does not adequately focus the light having passed through the capillary core to spatially separate it from the light having passed only through the capillary walls. During an experiment the image from the whole CCD was read into the computer for each exposure; for this experiment an area of 32×1024 pixels contained the image of the four capillaries; the remainder was discarded to conserve computer memory. The data was further reduced by adding together the pixel values in groups of four down the capillary length to give a total of 32×256 effective pixels for each snapshot; each effective pixel has 16 bit resolution and dimensions of 26×104 µm.

Exposure Referencing

Fluctuations in exposure times and in the light source intensity that is in excess of shot noise need to be accounted for in order to get the best possible performance from the detector. This is usually achieved by using a double beam arrangement, where a portion of the light from the source that does not pass through the sample is monitored and used as a reference. The ratio of this reference and the light that does pass through the sample is used to calculate the absorbance. In this experiment the light that strikes the CCD having passed only through the capillary walls is used as the reference. The electrophoresis of 4-nitrophenol in its ionic form was used to test the performance of the detection system. An optical filter with a center wavelength of 405 nm and bandpass of 10 nm was placed at the input to the fiber optic to match the absorbance wavelength of 4-nitrophenol at pH 7.5 (absorbance coefficient, $\epsilon_{405}$=1700 m$^2$ mol$^{-1}$). To establish which of the image pixels were to be used as 'reference pixels' and which to use as 'sample pixels' snapshots with the capillaries filled with water were compared with those with the capillaries containing a 1 mM solution of 4-nitrophenol. The average pathlength is $\pi d/4$=79 μm; this corresponds to absorbance of 0.13 AU for this solution. The pixels that showed a reduction in signal in the presence of the 4-nitrophenol solution that corresponded to an absorbance of <0.02 were used as reference pixels, those with >0.1 were used as sample pixels.

Capillary Electrophoresis and Data Processing

A series of parallel capillary electrophoresis experiments were carried out using a pH 7.5, sodium phosphate buffer (15 mM sodium) on dilutions of a 4-nitrophenol solution made up in buffer. Injections were performed inserting the inlet end of all the capillaries into the sample solution that was held at 2 cm above the level of the buffer in the outlet vial for 15 s. The volume injected into each capillary by siphoning should be approximately 16 nL. A voltage of +5 kV was applied to the inlet vial and the electrophoresis was carried out; electroosmotic flow ensured that the analyte moved towards the grounded cathode at the outlet. The snapshot data was accumulated in the computer RAM during the experiment and saved to disk at the end of a run.

The raw data collected during an experiment was first corrected for fixed pattern noise as described in detail in "A charge coupled device array detector for single-wavelength and multi-wavelength ultraviolet absorbance in capillary electrophoresis", Bergstrom and Goodall, Pokric and Allinson, Anal. Chem. 1999, 71, 4376-4384, and then processed to produce a set of electropherograms, one for each capillary. This ensures that high spatial resolution is maintained, limited only by the dimensions of the effective pixels used, 106 μm in this case.

Figure 9:
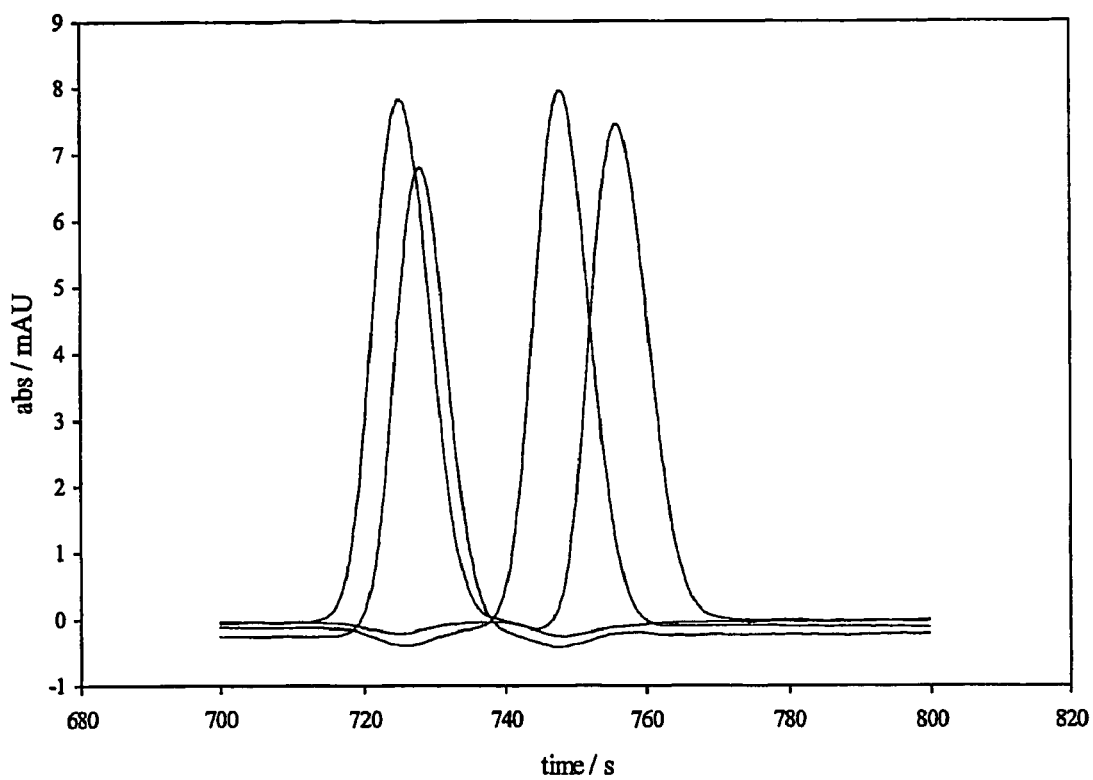
FIG. 9 shows electropherograms of ~16 nL of 100 microM 4-nitrophenol injected into each of four parallel 100 µm i.d. capillaries. Capillary length: 500 mm total, 300 to the detector. Separation voltage: 5000 V. Buffer: sodium phosphate pH 7.5 (15 mM sodium).
Figure 10:
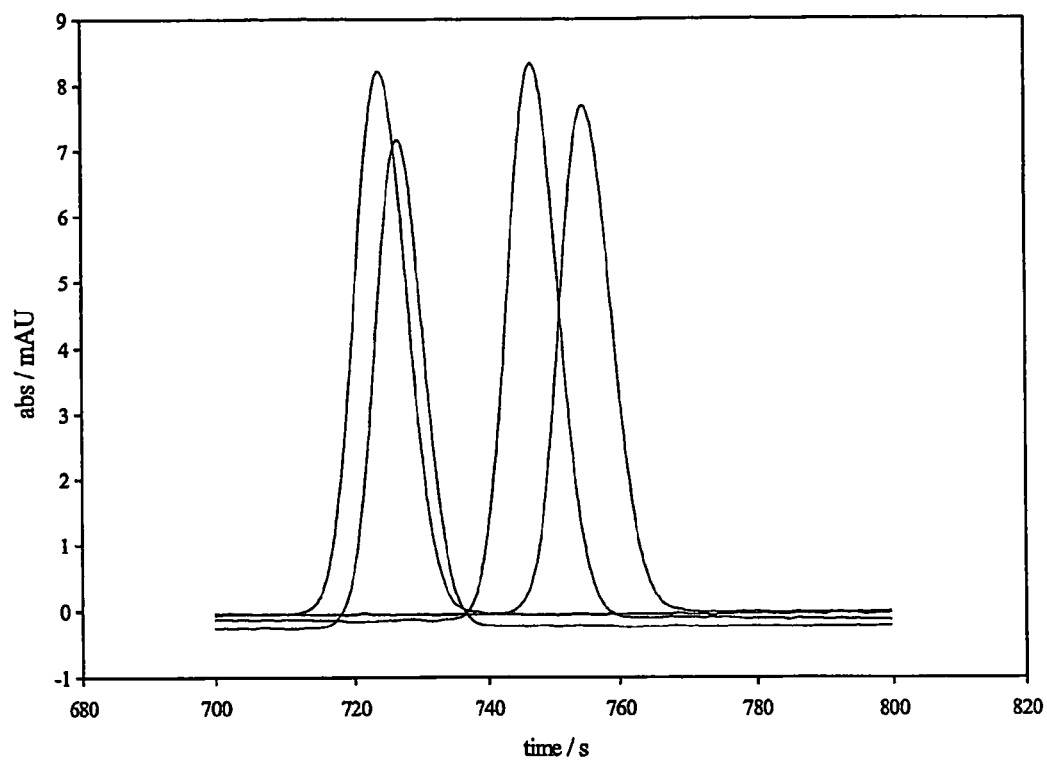
FIG. 10 shows electropherograms of 100 microM 4-nitrophenol after correction for cross-talk between capillaries.

FIG. 9 shows the four electropherograms obtained using a sample solution of 100 μM. It is clear from the dips in the base line at times corresponding to peaks in adjacent capillaries that there is cross talk between capillaries. This is mainly caused by some light passing through the sample being used as part of the reference, and to a lesser extent there is some light that after passing through the sample in one capillary lands on a sample pixel of an adjacent capillary. The extent of both of these effects has been measured by filling each capillary in turn with the sample solution. It has been assumed that the level of cross talk scales linearly with absorbance and the correction based on the measurement at this single sample concentration has been applied to all subsequent experiments. The appropriate correction is readily made as is demonstrated by FIG. 10.

Noise Performance

Figure 11:
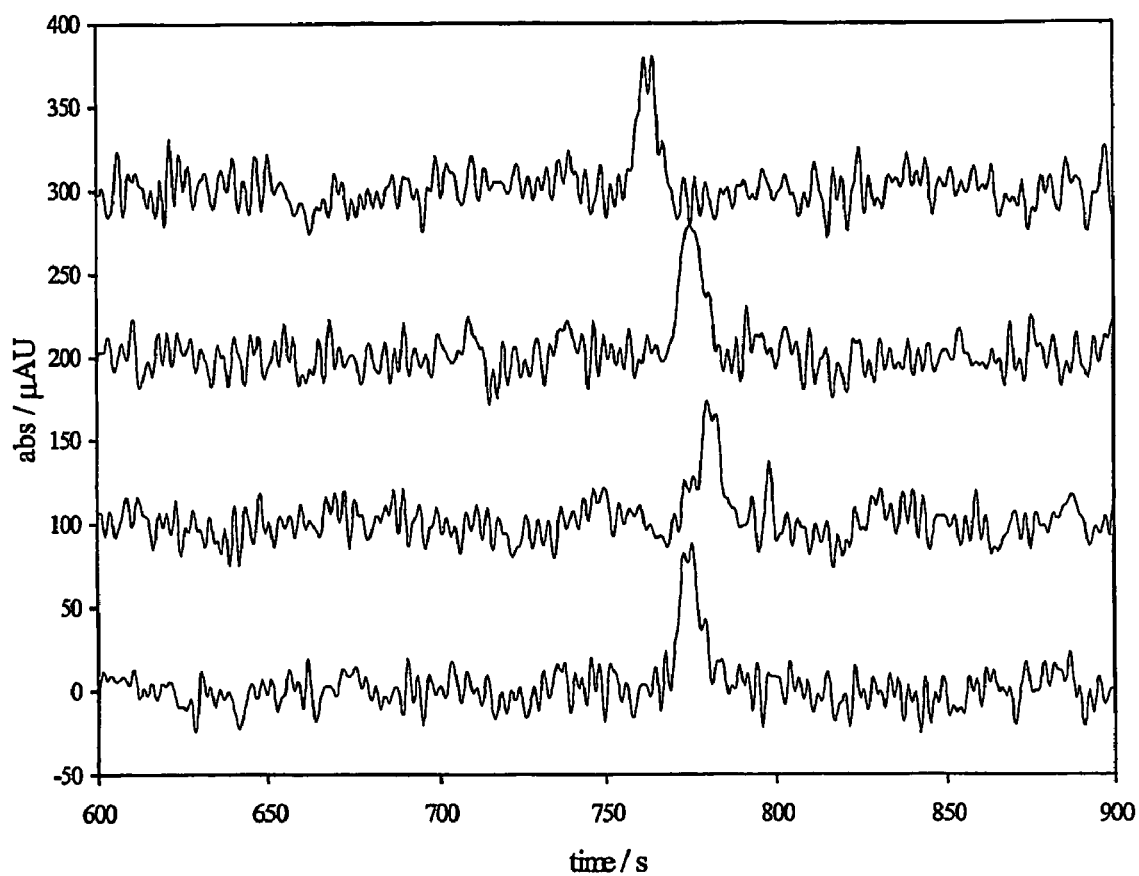
FIG. 11 shows electropherograms of ~16 nL of 1 microM 4-nitrophenol injected into each capillary.

FIG. 11 shows the four electropherograms obtained by injecting a solution of 1 μM 4-nitrophenol. The peak heights in FIG. 11 correspond to a concentration of ~0.6 μM, the limit of detection is calculated to be 0.22 μM based on three times the RMS baseline noise of 9.4 μAU (1 s risetime). The theoretical shot noise limited baseline noise level was calculated by generating simulated data sets based on the average exposure patterns and levels found in the experiment and assuming a pixel full well capacity of 5×10$^5$ electrons. These generated snapshot data sets were processed identically to the experimental data sets; the RMS shot noise level was found to be 9.0 μAU. This is very close to the observed value and indicates that the detector is shot noise limited.

Figure 12:
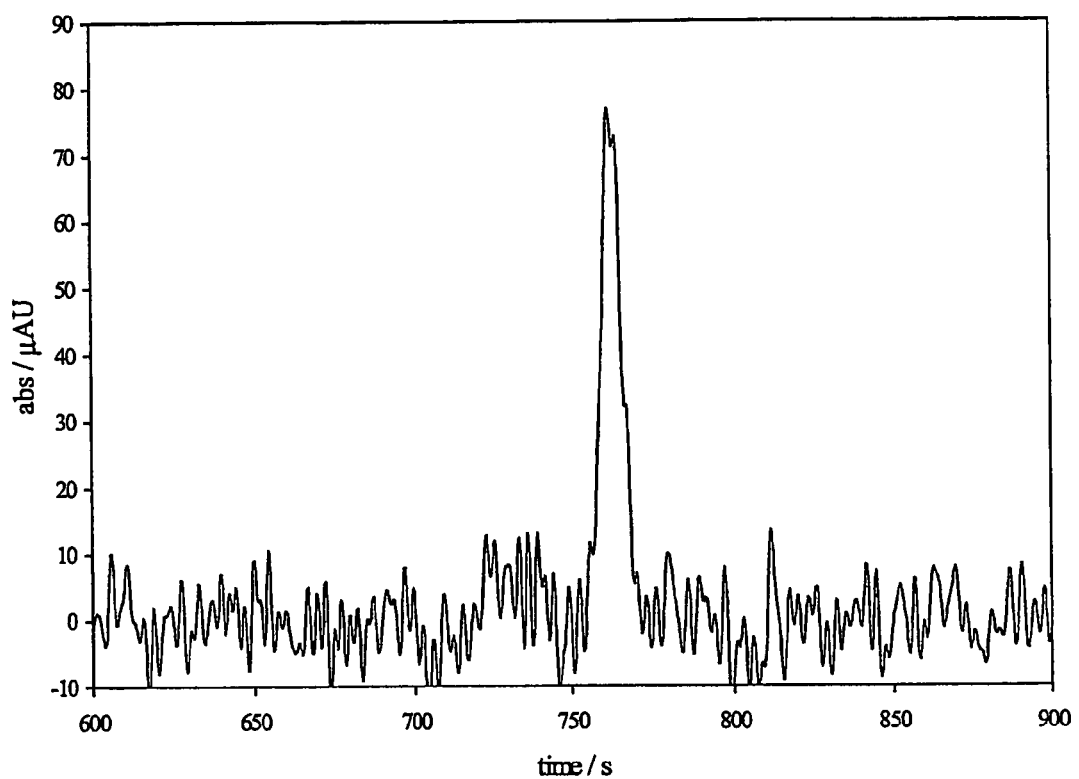
FIG. 12 shows an electropherogram generated by taking the average of the four traces shown in FIG. 11.

The CCD used in this experiment is large enough to accommodate over 30 capillaries aligned as the four are here. The sensitivity of detection for each of these capillaries would be the same as found in this study (i.e. ~9 μAU RMS noise with a rise-time of 1 s). Alternatively over 120 capillaries could be accommodated if they were aligned parallel to the short dimension of the CCD; this would result in a reduction in the signal integration time for each capillary by a factor of four and therefore an increase in noise level by a factor of $\sqrt{4}$=2. Capillary electrophoresis with arrays of capillaries obviously has application for high throughput analysis as the number of separations that can be carried out simultaneously simply scales with the size of the array. However, if the same sample is simultaneously injected into all the capillaries in the array, as done in this experiment, it is a means to increase sample loading and therefore dynamic range and concentration sensitivity. If all of the electropherograms are combined by taking the arithmetic average after compensation for the slight differences in analyte velocities between capillaries, then an increase in signal to noise of $\sqrt{N}$ is achieved, where N is the number of capillaries. Splitting a large sample load into many capillaries reduces the problems associated with overloading which include poor peak shape induced by electromigration dispersion and large injection lengths, and nonlinear detector response at high absorbances of highly abundant components. FIG. 12 shows the result of averaging the four electropherograms of FIG. 11. The RMS baseline noise level is 4.7 μAU, a reduction by a factor of 2 of the individual traces, this is the improvement expected for 4 capillaries.

The noise performance measured by combining the signal from four capillaries is still at the shot noise limit and is better than the performance achieved previously in Bergström et al above, where it was suggested that fluctuations in the spatial distribution of the lamp discharge, which is imaged on the fiber bundle input, would result in fluctuations in the spatial distribution of the CCD illumination. This would result in a noise level that is in excess of the shot noise because separate areas of the CCD monitor the signal and reference levels. Using a single optical fiber instead of the fiber bundle used previously should to a large degree scramble any spatial inhomogeneities of the lamp discharge. Scaling up the experiment to 30 parallel capillaries should give a combined RMS baseline noise level of 1.7 μAU, corresponding to an on column 4-nitrophenol concentration LOD of 40 nM.

When the analyte concentration is low relative to the concentration of background electrolyte then it should only be the length of the injection plug and analyte diffusion that contribute significantly to the measured peak width, assuming that the spatial resolution of the detector is high. The peak variance caused by analyte diffusion can be calculated, $\sigma^2 = 2Dt = 1.2 \times 10^{-6}$ m$^2$, where D is the diffusion coefficient ($8.1 \times 10^{-10}$ m$^2$ s$^{-1}$ for 4-nitrophenol) and t is time. The contribution to the peak variance from the length of the plug of sample injected is given by $l_i^2/12 = 0.4 \times 10^{-6}$ m$^2$ (where $l_i$ is the injection length of 2.0 mm). These two contributions give a total standard deviation, σ, of 1.3 mm; dividing by the analyte velocity gives σ=3.2 s in units of time. This compares well with a standard deviation of 3.1 s measured by fitting a Gaussian function to the peak in FIG. 12. This is experimental evidence that the detection method of imaging a 26.6 mm capillary section and of subsequently combining parallel electropherograms does not degrade separation efficiency.

EXAMPLE 2

TABLE 1

Table showing, for vessel with circular outer and inner cross sections, minimum values of ratio of the outer wall to detector distance d and the outer diameter of the vessel o.d. (d/o.d.) in order to obtain spatial separation between core and wall beams. Values are shown as a function of ratio of inner and outer diameters of the vessel (i.d./o.d.) for a range of solvents and vessel materials. Entries x indicate no spatial separation possible.

|  | i.d./o.d. 0.20 | i.d./o.d. 0.25 | i.d./o.d. 0.33 | i.d./o.d. 0.50 |
|---|---|---|---|---|
| Water/silica | x | 2.0 | 1.0 | 0.5 |
| Hexane/silica | 1.6 | 1.0 | 0.6 | 0.4 |
| Dichloromethane/silica | 0.6 | 0.5 | 0.4 | 0.2 |
| Water/polycarbonate | x | x | 2.1 | 0.5 |
| Water/flexible clear tubing (Tygon chemfluor 367) | 0.5 | 0.5 | 0.5 | 0.4 |

Values of refractive indices used in ray tracing analysis are: silica (1.458), water (1.333), hexane (1.375), dichloromethane (1.424), polycarbonate (1.585), Tygon chemfluor 367 (1.34). Other common reversed phase HPLC solvents, often used in admixture with water, are methanol (1.329) and acetonitrile (1.344): these and their mixtures will give similar values of d/o.d to water for the various vessel types. Hexane may be grouped with two other common normal phase HPLC solvents of comparable refractive index, 2-propanol (1.378) and ethyl acetate (1.372). The method used in constructing this Table is also effective for determining values for other solvents such as DMSO (1.479).

From the Table, for a known o.d. capillary the required i.d. can be determined from one of the possibilities to give a value of d/o.d. and thereby value of d, as described in the description.

EXAMPLE 3

Feedback Control

An example of feedback control is the use in a CE experiment for stopping the sample in the detection window, by turning off the voltage when it is detected as having migrated to the center of the window (see FIG. 13). After stopping, the subsequent broadening of the sample peak due to diffusion is monitored as a function of time. Analysis of the change in peak variance with time enables the diffusion coefficient to be determined. The hydrodynamic radius of the sample molecule may then be calculated using Stokes law. Combination of the diffusion coefficient with the mobility, obtained from the time taken to reach the window under a given field strength, enables the charge on the analyte to be deduced. Any starting peak shape is acceptable, since convolution of the peak with a Gaussian enables the Gaussian component of the peak broadening to be extracted. Whilst the example shows peak broadening measured over a period of 30 minutes, data quality is such that diffusion coefficients could be measured with good precision in less than 3 minutes.

Figure 14:
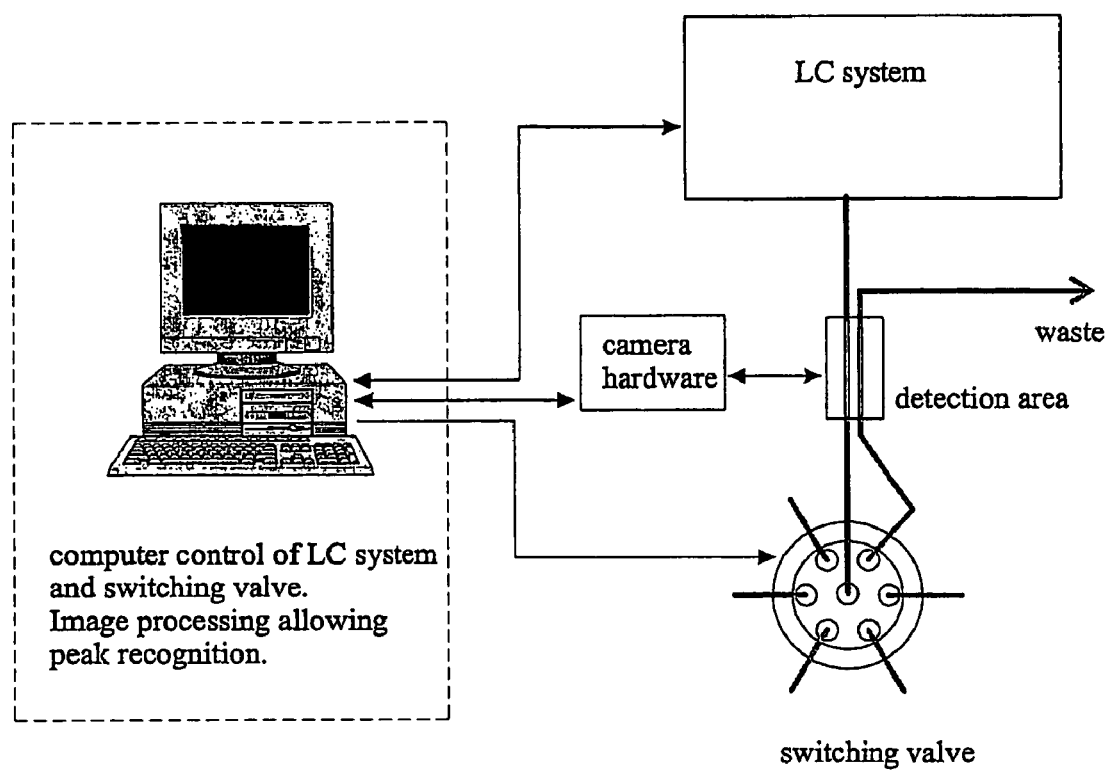
FIG. 14 shows a schematic of a possible arrangement for closed loop feedback control. The output from a liquid chromatography system is monitored during a first pass of the area detector. Peak recognition and decision making software can instruct the switching valve to direct the appropriate fraction for collection or for example to a mass spectrometer interface. After the appropriate switch the eluent is monitored again in a second pass of the detector so that the efficiency of the switching process can be monitored. An alternative would be to have more of the outputs from the switching valve passing the detector for visualization.

A schematic example of closed-loop feedback control is given in FIG. 14. Here the output from an LC system is monitored during a first pass of the area detector. Peak recognition and decision making software is used to instruct the switching valve to direct the appropriate fraction for collection or for example to a mass spectrometer interface. After the appropriate switch the eluent is monitored again in a second pass of the detector, so that the efficiency of the switching process can be monitored. An alternative is to have more of the outputs of the switching valve passing the detector for visualization.

EXAMPLE 4

Uses

Figure 15:
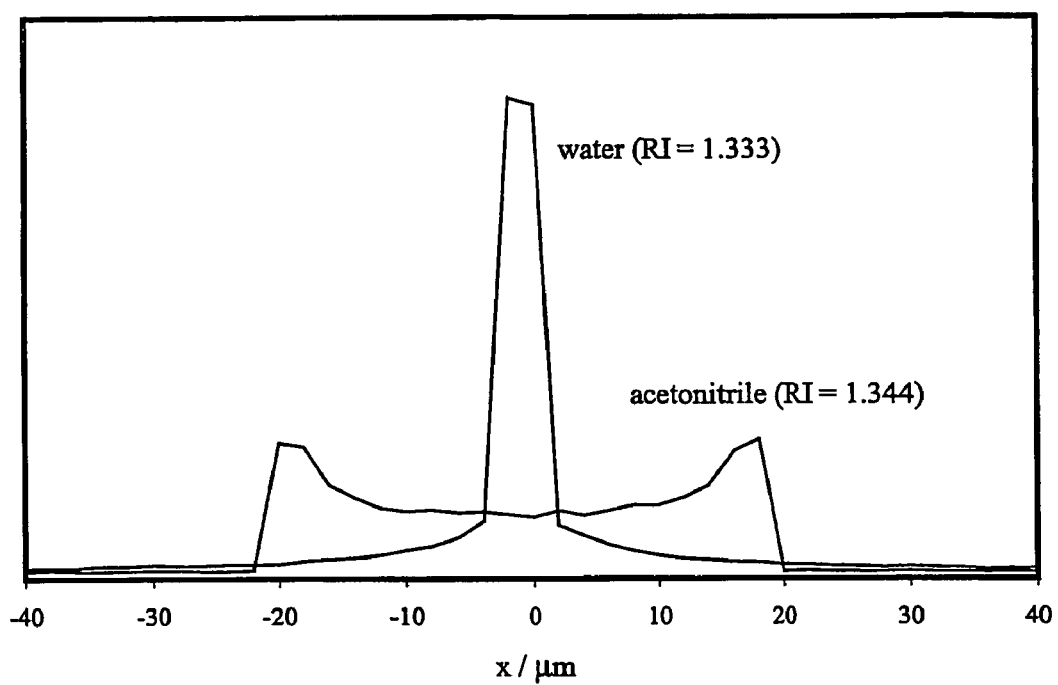
FIG. 15 shows as illumination pattern perpendicular to the capillary axis created by light passing through the core of a 75 µm i.d., 194 µm o.d. capillary, positioned 260 µm from the detection surface. Plots are shown for the capillary containing water and acetonitrile (at 20° C., sodium D line); the difference in the illumination pattern would allow the direct determination of the mobile phase composition during a gradient elution separation. Acetonitrile at 44° C. has the same refractive index as water does at 20° C.; the same approach could be used to determine the mobile phase velocity by applying a heat pulse upstream of the detector.
Figure 16:
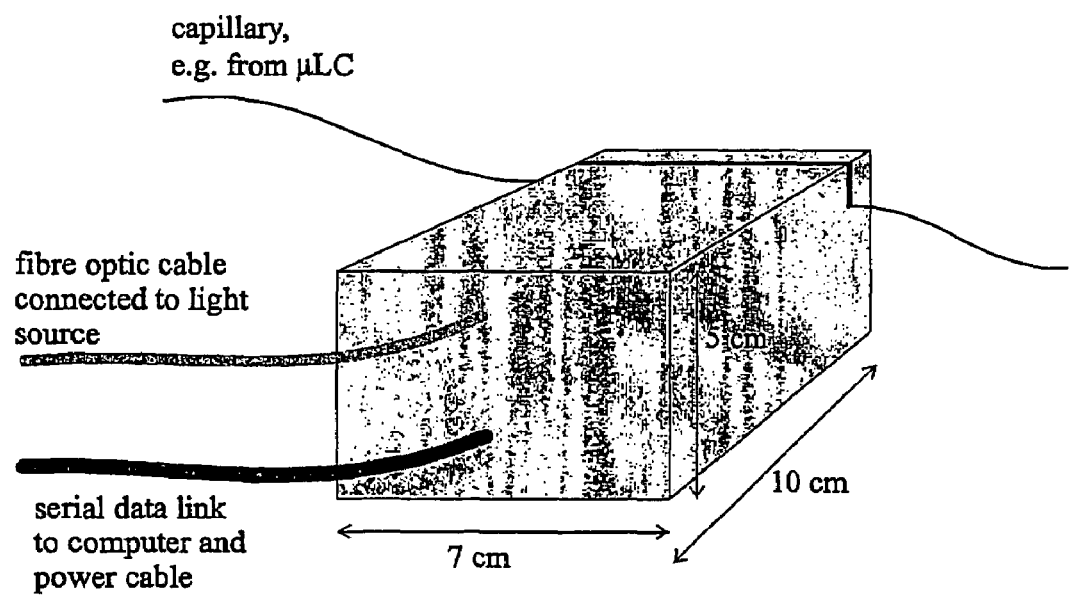
FIG. 16 is a diagram showing an optical assembly clip-on device of the invention showing the approximate dimensions for absorbance detection according to the invention, such as CE or absorbance. A module device of the invention would differ by comprising a capillary with interfacing means to insert into a capillary e.g. from a microLC or into a mass spectrometer.

The detection method of the invention is used in measuring refractive index change. By analysis of the illumination pattern of the core beam at high spatial resolution perpendicular to the capillary axis, the detector has the ability to monitor refractive index change in the solvent in the capillary. FIG. 15 shows, for a 75 μm i.d., 194 mm o.d. capillary positioned 260 μm from the detector surface, the change in profile of the core beam on changing from water (refractive index 1.333) to acetonitrile (refractive index 1.344). With a pixel size of 10 μm, this would allow distinction between the two illumination profiles, and by extension the ability to directly monitor the mobile phase composition during a gradient elution separation in water-acetonitrile mixtures. If necessary, magnification in the direction perpendicular to the capillary axis could be used to increase the resolution in terms of mobile phase composition. This would be of benefit in HPLC. Since acetonitrile at 44° C. has the same refractive index as water does at 20° C., application of a heat pulse providing a 25° C. temperature rise up-stream of the detector could be used to determine the mobile phase velocity in capillary HPLC.

Another use of multicapillary absorbance detection is for rapid measurement of $pK_a$. Here aliquots of the sample solution are mixed into a set of buffer solutions covering a range of pH values, typically spanning the range 2-12, and all mixtures are then drawn up into separate capillaries in the sequence buffer then mixture of buffer plus sample. By taking measurements at one or more wavelengths where acid and base forms have different absorbance, results from all capillaries of absorbance as a function of pH may be processed to determine $pK_a$ values. Using suitable non- or weakly-absorbing inorganic buffers, this is applicable for organic or biological compounds containing all common titratable functional groups, including carboxyl and amine groups, and at concentrations down to 100 micromolar. This is of benefit in for example the pharmaceutical industry and for high throughput screening.

The invention claimed is:

1. An optical assembly comprising a light source, at least one sample vessel and a detector, the at least one vessel being positioned in a light path or paths created between the source and the detector in manner to enable transmission of light through the vessel wherein the light source is adapted to provide a beam of substantially collimated light, the detector comprises a plurality of detector locations and the vessel comprises a wall and core of relative shape and dimensions adapted to contain a sample for detection and to define at least two spatially separated transmitted light paths, a first wall path which enters and exits the vessel walls only, spatially separated from a second core path which enters and exits the vessel walls and additionally the vessel core, wherein the spatially separated wall and core paths are coupled to individual detector locations on the detector, and the detector is an array detector.

2. Optical assembly of claim 1 wherein the assembly defines a central core path and two peripheral wall paths either side thereof or an annular wall path thereabout.

3. Optical assembly of claim 1 wherein core and wall path beams are spatially close, preferably adjacent, on the array detector, facilitating direct referencing as the ratio of the core beam to the wall beam.

4. Optical assembly of claim 1 wherein the light source comprises at least one wavelength of light that is absorbed by one or more absorbing species comprised in the sample for detection, the absorbance of which is to be detected.

5. Optical assembly of claim 1 wherein light is of wavelength in the range 160 to 1200 nm, preferably 180 or 190 to 1200 nm, corresponding to UV, UV-vis to near infra red (NIR).

6. Optical assembly of claim 1 wherein the at least one sample vessel in the assembly of the invention comprises a cell or conduit which is open ended and open based and topped, intended for dynamic sample detection.

7. Optical assembly of claim 1 wherein the sample vessel is a single cell or one of a plurality of cells in an array; or is a single capillary or one of a plurality of capillaries in a microcapillary array or a microfabricated channel array.

8. Optical assembly of claim 1 characterized by i.d.(inner diameter) (vessel) in the range 3 micron to 20 mm, o.d.(outer diameter) (vessel) in the range 4 micron to 30 mm, refractive index (vessel) in the range 1.3-<1.6, refractive index (sample) in the range 1.3 to in excess of 1.5, ratio d(outer wall to detector distance)/o.d. is 0.5 to 10 and d is in the range 20 micron to 300 mm.

9. Optical assembly of claim 1 wherein an array detector comprises a solid state sensing device, preferably a CCD, CID or a CMOS APS.

10. Optical assembly of claim 1 wherein an array detector comprises a CCD, CID or CMOS APS including a surface stud comprising a coating to absorb incident light and reemit at a different wavelength, to convert UV to visible light, to allow detection by the CCD, CID or CMOS APS wherein the coating is applied directly to the stud or to a cover slip interleaved between the stud and vessel, facilitating recoating as needed, by replacing the cover slip without need to replace the stud.

11. Optical assembly of claim 1 which comprises means for real-time signal processing for optimum peak detection and parameterization/characterization, and means for automatic system management including closed-loop feedback control of the apparatus and systems.

12. Optical assembly of claim 11 in which closed-loop feedback control means includes means for stopping or slowing the flow following initial observation in the detection means to allow sample to reside in the detector window and give longer times for data acquisition and enhanced signal to noise or to enable fraction collection, or to direct a fraction to an analysis means.

13. Optical assembly of claim 1 which is a module for use with a column or capillary separating device as known in the art, wherein the vessel is a capillary or column comprising interfacing means at one end for inserting into the outlet of a column or capillary separating device or along the length thereof, the capillary or column optionally comprising interfacing means enabling insertion into the inlet of an analyzing means at the other end; or is a clip-on device comprising means for locating about a section of a capillary or column separating device which is of suitable i.d, o.d. and refractive index as hereinbefore defined and is stripped of any surface coating to facilitate the operation of the method of the invention, whereby the stripped capillary or column provides the sample vessel of the assembly.

14. Optical assembly as hereinbefore defined in claim 1 for use in the pharmaceutical, biomedical and bioscience, agrochemical, veterinary and materials fields, for detection, analysis, characterization and quantification of samples contained in a vessel, and optionally further collecting separated components thereof.

15. Apparatus for chemical reaction or synthesis and analysis or for sample separation or transport wherein the apparatus comprises the optical assembly of claim 1 as hereinbefore defined in which the chemical reaction vessel itself is cylindrical and the reaction monitored in batch flow mode as a function of time, and feedback control used to halt reaction or in which the reaction vessel is tubular and used in continuous flow mode.

16. Method for detection of light transmitted through at least one sample contained within the core of at least one sample vessel of an optical assembly as hereinbefore defined in claim 1, comprising illuminating the vessel with a substantially collimated light source or sources and detecting transmitted light in an array detector, wherein transmitted light is spatially separated into at least two light paths, a wall path which has passed through the vessel walls only, spatially separated from a core path which has passed through the walls and core, wherein the spatially separated light beams are coupled to individual detection locations on the array detector.

17. Method of claim 16 wherein a sample includes one or a plurality of analytes which it is desired to detect in the course of a chemical reaction generating or consuming a species as analyte.

18. Method of claim 16 which additionally comprises selecting a sample for analysis, determining individual wavelengths at which absorption by desired sample components is strongest, checking refractive index of the sample in order to select a suitable sample vessel which when containing the sample and when illuminated will generate spatially separated beams as hereinbefore defined or selecting a suitable combination of optical components and filters and a suitable vessel to detect an array separation to couple spatially separated beams to independent locations on the detector array.

19. Method of claim 16 in which sample is introduced into the at least one sample vessel by injection, loop injection, pipette, hydrostatic, or electrokinetic injection and is removed from the vessel by injection, electrospray or interface for discard or to a further vessel for storage or to a down stream identification means.

20. Method of claim 16 which comprises referencing the light detected by the detection means by means of exposure referencing wherein the ratio of the core beam intensity to the wall beam intensity gives a value for the sample intensity at each location with elimination of excess or flicker noise due to light source fluctuation.

* * * * *